(12) United States Patent
Adachi et al.

(10) Patent No.: US 7,767,147 B2
(45) Date of Patent: Aug. 3, 2010

(54) SUBSTRATE FOR TRANSPORTING LIQUID, A SYSTEM FOR ANALYSIS AND A METHOD FOR ANALYSIS

(75) Inventors: Sakuichiro Adachi, Hachioji (JP); Kunio Harada, Hachioji (JP); Hideo Enoki, Kasumigaura (JP); Hironobu Yamakawa, Toride (JP); Tomonori Mimura, Tomobe (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1107 days.

(21) Appl. No.: 11/258,230

(22) Filed: Oct. 26, 2005

(65) Prior Publication Data

US 2006/0097155 A1    May 11, 2006

(30) Foreign Application Priority Data

Oct. 27, 2004  (JP) ............................. 2004-311716

(51) Int. Cl.
*G01N 21/00* (2006.01)
*G01N 1/10* (2006.01)
*B01L 3/00* (2006.01)
*B01L 3/02* (2006.01)

(52) U.S. Cl. ........................... 422/63; 422/99; 422/100; 436/180

(58) Field of Classification Search .................. 422/63, 422/99, 100
See application file for complete search history.

(56) References Cited

U.S. PATENT DOCUMENTS

| | | | |
|---|---|---|---|
| 6,565,727 | B1 | 5/2003 | Shenderov |
| 2001/0041357 | A1 | 11/2001 | Fouillet et al. |
| 2003/0183525 | A1 | 10/2003 | Elrod et al. |
| 2004/0007377 | A1 | 1/2004 | Fouillet et al. |
| 2004/0055891 | A1 | 3/2004 | Pamula et al. |

FOREIGN PATENT DOCUMENTS

| | | |
|---|---|---|
| JP | 60-216324 | 10/1985 |
| JP | 7-506340 | 7/1995 |
| JP | 7-506430 | 7/1995 |

(Continued)

OTHER PUBLICATIONS

"Electrowetting-Based On-Chip Sample Processing for Integrated Microfluidics" by Fair, et al. IEEE Inter. Electron Devices Meeting 2003.

(Continued)

*Primary Examiner*—Jill Warden
*Assistant Examiner*—Dean Kwak
(74) *Attorney, Agent, or Firm*—Mattingly & Malur, P.C.

(57) ABSTRACT

Conventional liquid transport substrates having a fluid channel formed along an array of electrodes have a problem in which throughput decreases, depending on driving conditions. In order to avoid two-way passage in a fluid channel from the inlet to a measuring section and a fluid channel from the measuring section to the outlet, the measuring section is located in the middle of the fluid channel connecting the inlet and the outlet, so that manipulation from the inlet to the outlet takes place in one direction on the substrate. Even when analyzing a large number of sample droplets, by transport of the droplets substantially in one direction, it is possible to complete measurement in a short time.

18 Claims, 18 Drawing Sheets

FOREIGN PATENT DOCUMENTS

| | | |
|---|---|---|
| JP | 10-267801 | 10/1998 |
| JP | 2004-000935 | 1/2004 |
| JP | 2004-022165 | 1/2004 |
| WO | WO 93/22053 | 11/1993 |
| WO | WO 02/23163 | 3/2002 |
| WO | WO 03008931 A2 * | 1/2003 |
| WO | WO 2004/030820 | 4/2004 |

OTHER PUBLICATIONS

Clinical Diagnostics on Human Whole Blood, Plasma, Serum, Urine, Saliva, Sweat, and Tears on a Digital Micrcofluidic Platform, by Srinivasan, et al. µTAS 2003.

Carrier-Based Ion-Selective Electrodes and Bulk Optodes. 1. General Characteristics, by Eric Bakker, et al. Chem. Rev. 1997, 97, 3083-3132.

Srinivasan et al., "An integrated digital microfluidic lab-on-a-chip for clinical diagnostics on human physiological fluids," Lab On a Chip, Royal Society of Chemistry, Cambridge, GB, vol. 4, No. 4, May 2004, pp. 310-315, XP002353247.

Pollack et al., "Electrowetting-Based Actuation of Droplets for Integrated Microfluidics", Lab On a Chip, Royal Society of Chemistry, Cambridge, GB, vol. 2, No. 2, Mar. 2002, pp. 96-101, XP008038786.

Masao, "Electrostatic Actuation of Liquid Droplets for Microreactor Applications", IEEE Transactions on Industry Applications, IEEE Service Center, Piscataway, NJ, US, vol. 34, No. 4, Aug. 1998, XP011022429.

Cho et al., "Creating, Transporting, Cutting, and Merging Liquid Droplets by Electrowetting-Based Actuation for Digital Microfluidic Circuits", Journal of Microelectromechanical Systems, IEEE Service Center, Piscataway, NJ, US, vol. 12, No. 1, Feb. 2003, pp. 70-80, XP003006917.

* cited by examiner

SUBSTRATE FOR TRANSPORTING LIQUID, A SYSTEM FOR ANALYSIS AND A METHOD FOR ANALYSIS

CLAIM OF PRIORITY

The present application claims priority from Japanese application JP 2004-311716 filed on Oct. 27, 2004, the content of which is hereby incorporated by reference into this application.

FIELD OF THE INVENTION

The present invention relates to an analysis system that transports a liquid on a substrate and measures the conditions of the liquid and the amounts of ingredients of the liquid. In particular, the invention relates to such an analysis system that is required to carry out high-throughput processing.

BACKGROUND OF THE INVENTION

Recently, reaction liquids for use in analysis systems which measure the amounts of ingredients of a sample liquid have been required to be more minute quantities to reduce reagent cost and reduce environmental burdens. Current analysis systems dispense a sample liquid and a reagent into plastic or glass reaction solution vessels, mix them to prepare reaction solutions, and measure the amounts of ingredients by measuring the intensity of light emitted from or transmitted through the reaction solutions. When preparing more minute quantities of reaction solutions in the current analysis systems, the liquids become harder to handle and bubbles are generated during the dispensing and mixing process. This has posed a problem in which accurate measurements cannot be achieved. For this reason, techniques of microfluidic liquid handling with accuracy have been required.

As a technique of microfluidic liquid handling, a method that transports a liquid on a substrate under electrical control has lately attracted attention. In this method, generally the following two manners are used. A first manner is such that liquid droplets to be transported are sandwiched between two opposing substrates having a plurality of electrodes and the droplets are driven by applying voltage to electrodes arranged along the surfaces of the two opposing substrates (e.g., [patent document 1]). Typically, a great number of electrodes are arranged on one substrate along a fluid channel through which a liquid is allowed to move and the other substrate has a single electrode formed over its surface and connected to ground. When a liquid droplet stands still across some electrodes and voltage is applied to one of these electrodes under the droplet, the droplet in contact with the electrode to which the voltage is applied comes to have a good wetting behavior and eventually moves to just above that electrode by electrocapillarity (e.g., [patent document 2]). By repeating this, the droplet is transported.

Another manner is such that a liquid droplet to be transported is supplied to enter a channel on a single substrate with a great number of electrodes and the droplet is driven by applying voltage to an electrode near the droplet (e.g., [patent document 3]). The electrodes are arranged along the fluid channel through which a liquid is allowed to move. By forming an electric field between an electrode lying under the droplet and an electrode near the droplet and utilizing the force of the electric field, the droplet is driven. By repeating this, the droplet is transported.

Both these manners are capable of transporting microfluidic liquid. In these manners, by moving two microdroplets of liquids to a same electrode, the microdroplets can be mixed and it is also possible to divide one microdroplet into two parts. These systems in which a microfluidic liquid is transported and analyzed by switching one electrode to another to which voltage is applied on the substrate having an array of electrodes have the following advantages. Because a single or two substrates are used, samples are less liable to be affected by bubbles than a vessel with side walls. Simply applying voltage to the electrodes, a large number of microdroplets can be driven individually wherever on the substrate. Because a position in which a microdroplet is placed can be determined by applying voltage to a certain electrode, if measurement is performed by a measuring section provided to obtain information from a sample, timing when the sample droplet or reaction solution arrives at the measuring section can be set easily. Analysis systems devised and built by substrate technology have been reported (e.g., [non-patent document 1] and [non-patent document 2]).

In a typical example of analysis systems described in the above documents, there are a sample inlet section into which a sample droplet is inserted into the substrate, a mixing section where the sample liquid is mixed with a reagent, a measuring section for measurement, and an outlet section from which a reaction solution is ejected and these sections are connected by a fluid channel formed with a great number of electrodes. A sample liquid entered from the sample inlet section is mixed with a reagent in the mixing section and a reaction solution is prepared. After ingredients are measured in the measuring section, the reaction solution is transported back through the same fluid channel and ejected from the outlet section.

[Patent document 1] JP-A No. 216324/1985

[Patent document 2] JP-A No. 2004-000935

[Patent document 3] JP-A No. 267801/1998

[Patent document 4] JP-A No. 2004-22165

[Patent document 5] JP-A No. 267801/1998

[Non-patent document 1] R. B. Fair et al. "Electrowetting-based On-Chip Sample Processing for Integrated Microfluidics" IEEE Inter. Electron Devices Meeting 2003

[Non-patent document 2] Vijay Srinivasan et al. "Clinical diagnostics on human whole blood, plasma, serum, rine, saliva, sweat, and tears on a digital microfluidic platform" µTAS 2003

[Non-patent document 3] Eric Bakker, Philippe Buhlmann, and Erno Pretsch Chem. Rev. 1977, 97, 3083-3132

SUMMARY OF THE INVENTION

In the example typical of the analysis systems described in the above documents, no consideration is taken for analyzing a large number of sample droplets. A portion of the fluid channel to transport a sample droplet from the sample inlet section to the measuring section is shared to transport the sample droplet back from the measuring section to the outlet section. Therefore, two-way passage takes place in that portion of the microfluidic analysis route through which sample droplets are transported for analysis on the substrate. This is because the fluid channel is routed in a compact and folded manner on the substrate to reduce device size. However, when a large number of sample droplets are analyzed, until one droplet is measured and transported to the outlet section, the next droplet must stay in the channel portion of the inlet side before the two-way passage portion of the channel in the microfluidic analysis route. In consequence, a problem in which it takes very much time to complete analyzing all sample droplets has been posed. To avoid collision between a measured sample droplet and the next droplet to be measured or collision between a reagent and a reacted reaction solution, it is necessary to drive the droplets with a time lag, which has posed a problem of throughput decrease. An object of the present invention is to provide a small device capable of analyzing a great number of samples at high throughput.

In accordance with the above object, a system for transporting a liquid on a substrate having a plurality of electrodes by applying voltage to the electrodes is provided, the system comprising a first substrate, an inlet into which a liquid droplet is inserted, provided on the first substrate, an outlet from which the liquid droplet is ejected, provided on the first substrate, a plurality of electrodes provided on the first substrate, and an electrical conduction means to apply voltage at least part of the plurality of electrodes, wherein the plurality of electrodes form a fluid channel through which liquid droplets pass and a measuring section, wherein the fluid channel lies between the inlet and the outlet and the measuring section is located on at least a segment of the fluid channel. The measuring section is placed in the middle of the fluid channel connecting the sample inlet and the outlet and liquid manipulation takes place along one-way pipeline from the inlet to the outlet. A first channel from the inlet to the measuring section and a second channel from the measuring section to the outlet are straight, eliminating two-way passage in the microfluidic analysis route.

A schematic layout of an analysis system without a two-way passage in the microfluidic analysis route through which sample droplets are transported is shown in FIG. 1. The analysis system is comprised of a sample inlet 203, a measuring section 206, and an outlet 204, wherein the sample inlet 203 and the outlet 204 are connected by a fluid channel 205 allowing for transport of a sample 1 as a first liquid and a measuring section 206 lies in the middle of the channel. A large number of sample droplets from the sample inlet 203 are serially transported through the fluid channel 205 and measured in the measuring section 206, and then transported up to the outlet 204. Here, assuming that it takes one minute for a sample droplet to pass from the sample inlet 203 to the measuring section 206, one minute for measurement in the measuring section 206, and one minute for a sample droplet to pass from the measuring section 206 to the outlet 204, it takes three minutes (1+1+1=3) to complete analyzing one sample droplet. Because sample droplets are serially transported, it takes 12 minutes (1+1×10+1) to complete analyzing 10 sample droplets. Throughput of continuous operation for one hour is 50 droplets/hour.

On the other hand, a schematic layout of an analysis system with a two-way passage portion of the microfluidic analysis route through which sample droplets are transported is shown in FIG. 2. The analysis system is comprised of a sample inlet 203, a measuring section 206, and an outlet 204, wherein the sample inlet 203, measuring section 206, and outlet 204 are connected by fluid channel portions 205', 205", and 205'". Sample droplets from the sample inlet 203 are transported through a fluid channel portion 205', pass one by one through a fluid channel portion 205", measured in the measuring section 206, and go back through the fluid channel portion 205". Then, passing through a fluid channel portion 205'", the sample droplets are transported up to the outlet 204. Assuming that it takes 30 seconds to transport a sample droplet through each fluid channel portion 205', 205", 205'" and one minute for measurement in the measuring section 206, it takes three minutes (0.5+(0.5+1+0.5)+0.5)=3) to analyze one sample droplet. However, it takes 21 minutes (0.5+(0.5+1+0.5)×10+0.5)=21) to complete analyzing 10 sample droplets. Throughput of continuous operation for one hour is 30 droplets/hour. In the system without a two-way passage in the microfluidic analysis route, there is less possibility that contamination occurs due to collision of sample droplets by erroneous operation or the like, as compared with the system with a two-way passage in the microfluidic analysis route. Furthermore, in the present invention, a plurality of fluid channels having measuring sections are provided, sample droplets are distributed to each fluid channel, and parallel analysis processing is performed, thereby enhancing throughput.

This is effective especially for application to automatic analysis apparatus for clinical inspection required to have high throughput. Current automatic analysis apparatus includes a disk having reaction solution vessels arranged equiangularly in the rim and measures reaction solutions put in all reaction solution vessels one by one by a measuring instrument located in a place, while rotating the disk. In this manner, however, the number of reaction solution vessels that can be arranged on the disk is limited. Consequently, throughput is not improved much even if measuring instruments can be added. According to a manner of the present invention, by adding fluid channels having measuring sections, parallel analysis processing can be performed and it is possible to realize a compact device having higher throughput than the current automatic analysis apparatus.

According to the present invention, it is possible to realize a compact and high-throughput device. Even when analyzing a large number of sample droplets, by transport of the droplets substantially in one direction, it is possible to complete measurement in a short time.

DETAILED DESCRIPTION OF THE PREFERRED EMBODIMENTS

A first embodiment will be described below. In the first embodiment, serum is used as a sample liquid and a plurality of sample droplets are serially transported substantially in one direction on a substrate. The intensity of light transmitted through each sample droplet is measured in a measuring section and the turbidity of the sample droplet is measured.

Figure 1:
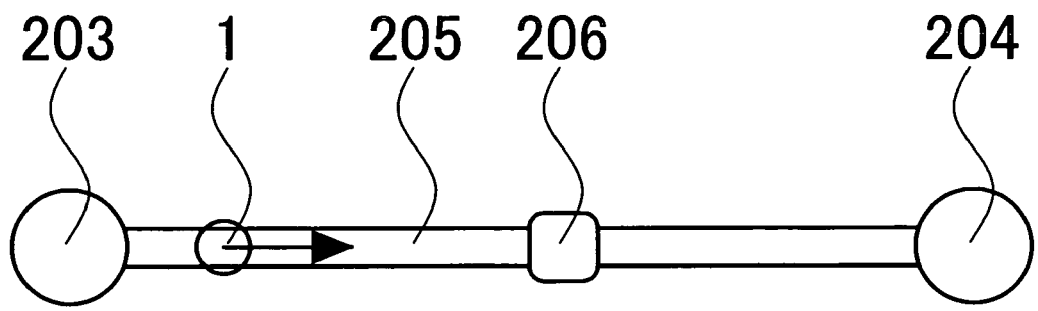
FIG. 1 shows an example of a schematic layout of an analysis system.
Figure 2:
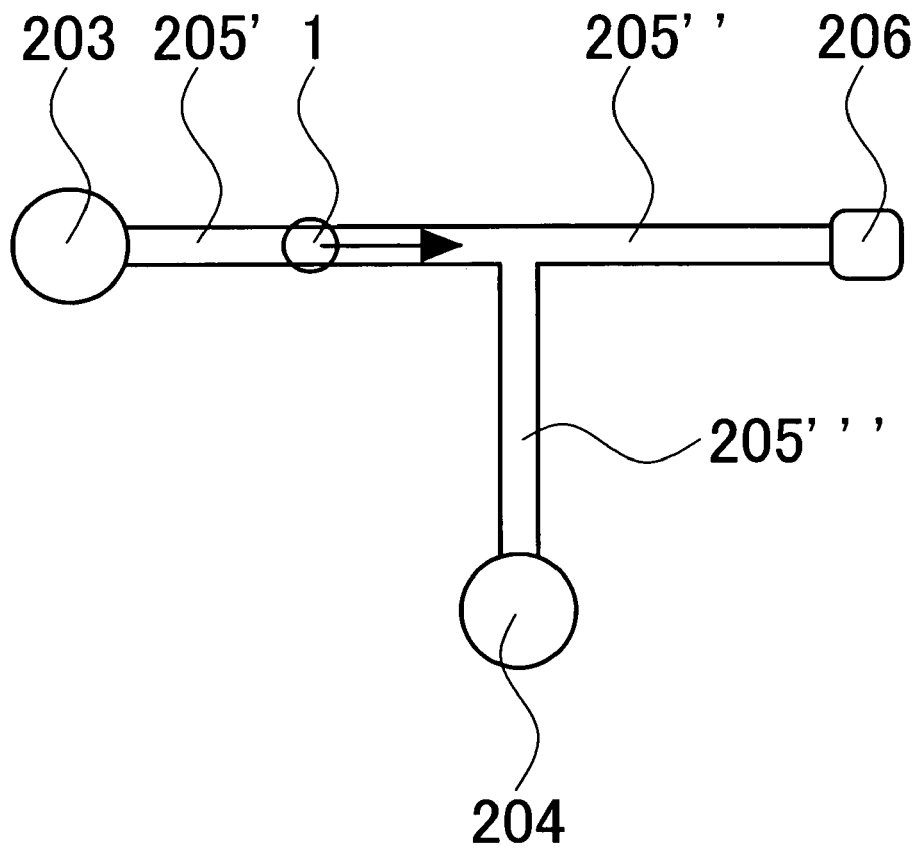
FIG. 2 shows an example of a schematic layout of another analysis system.
Figure 3:
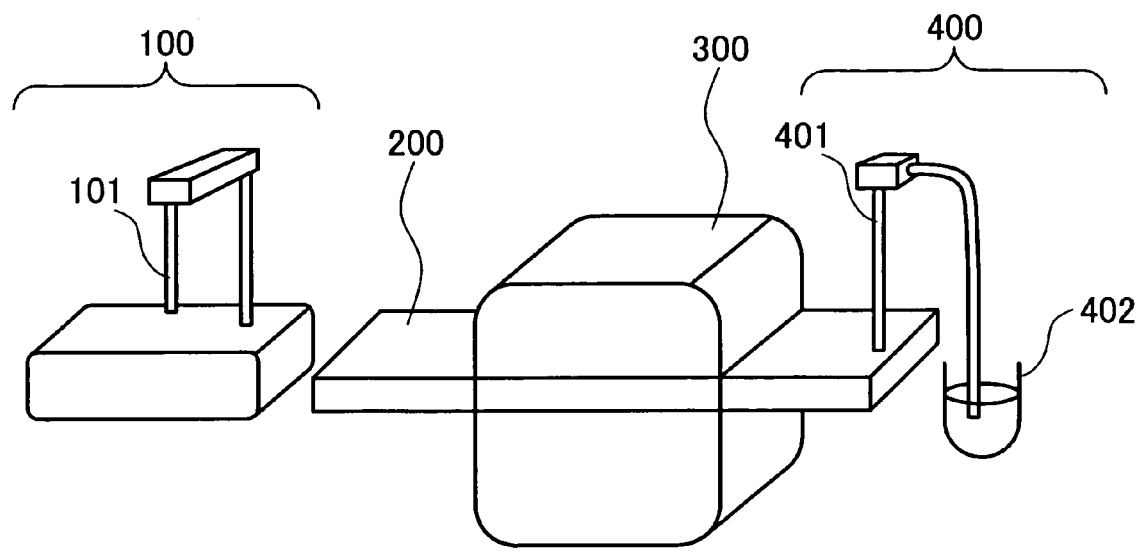
FIG. 3 is a schematic showing apparatus setup for a first embodiment of the present invention.

Apparatus setup is shown in FIG. 3. The apparatus is composed of a sample disk unit 100, a transport substrate unit 200, an optics unit 300, and a ejection unit 400. A sample droplet is dispensed from the sample disk unit 100 into the transport substrate unit 200 by a pipetter 101 included in the sample disk unit 100. The sample droplet is transported by applying voltage to electrodes serially, arranged on the inside of a substrate in the transport substrate unit 200. After subjected to sensing by the optics unit 300, the sample droplet is ejected from the transport substrate unit 200 by a sipper 401 included in the ejection unit 400 to an ejection tank 402.

Figure 4:
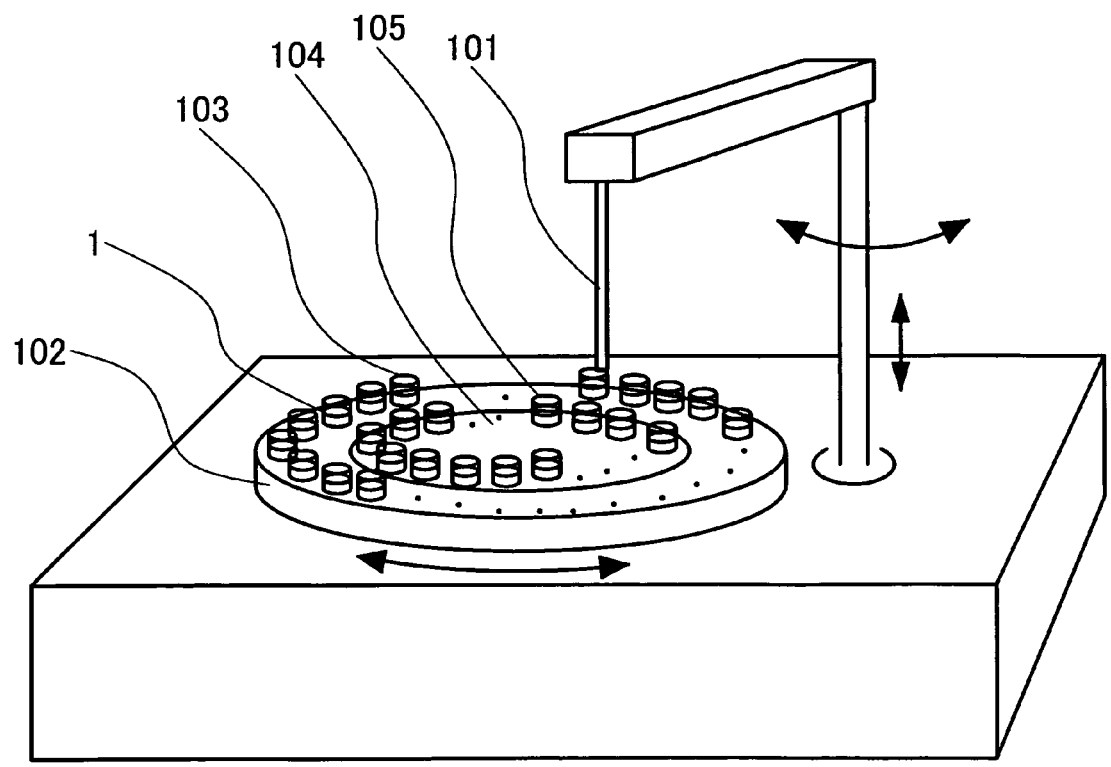
FIG. 4 shows a detailed view of a sample disk unit for the first embodiment of the present invention.

The construction of the sample disk unit 100 is shown in FIG. 4. Drops of the sample liquid 1 are contained in a plurality of vessels 103 arranged equiangularly in the rim of a sample disk 102. The sample disk 102 rotates by a motor. A preprocess disk 104 is placed to the inner perimeter of the sample disk 102 to dilute the sample liquid in a plurality of preprocess vessels 105 arranged thereon.

The pipetter 101 moves vertically and turns on a circle around its support rod. In time with the turning of the sample disk 102 and the preprocess disk 104, the pipetter 101 draws the sample liquid 1 from a vessel 103 and transfers it to a preprocess vessel 105 and draws the liquid from a preprocess vessel 105 and drops the reagent 1 as a first liquid into the transport substrate unit 200.

Figure 5:
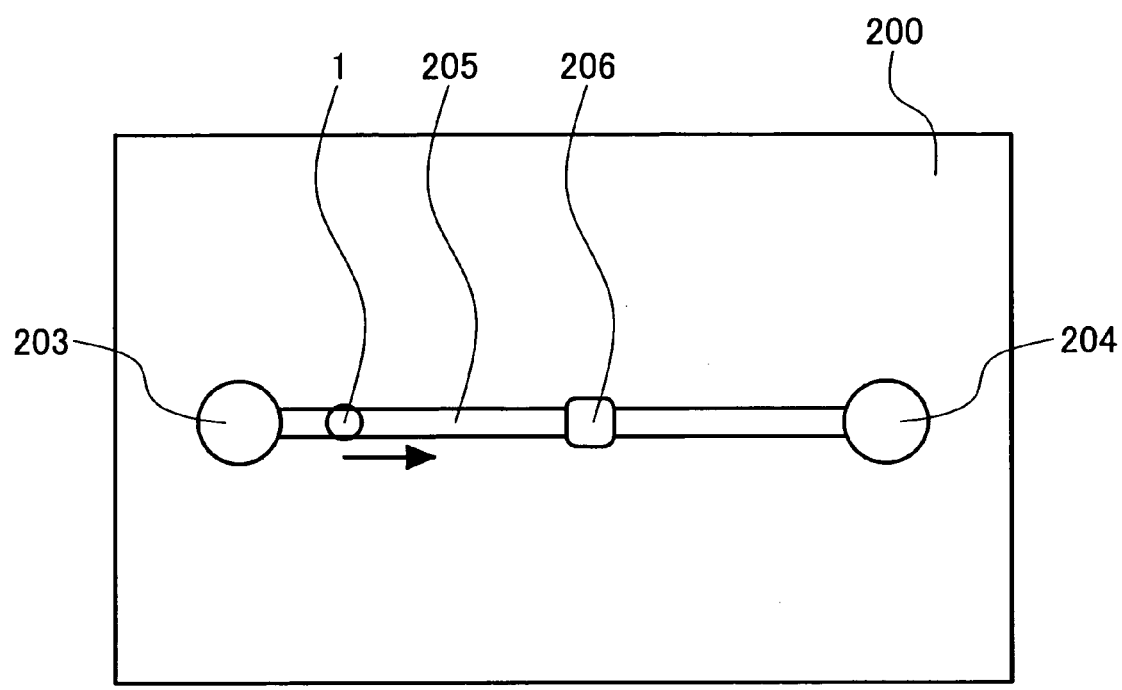
FIG. 5 shows a layout of the elements of a liquid transport substrate for the first embodiment of the present invention.

A schematic internal view of the transport substrate unit 200 is shown in FIG. 5. Inside the transport substrate unit 200, a sample inlet 203, a measuring section 206, and an outlet 204 are placed, wherein the sample inlet 203 and the outlet 204 are connected by a fluid channel 205 allowing for transport of the reagent 1 which is the first liquid and the measuring section 206 lies in the middle of the channel. A sample droplet 1 as the first liquid dispensed into the sample inlet 203 by the pipetter 101 is transported through the fluid channel 205, measured in the measuring section 206, and then transported up to the outlet 204. Then, the droplet is ejected by the sipper 401 included in the ejection unit 400 to the ejection tank 402.

Figure 6:
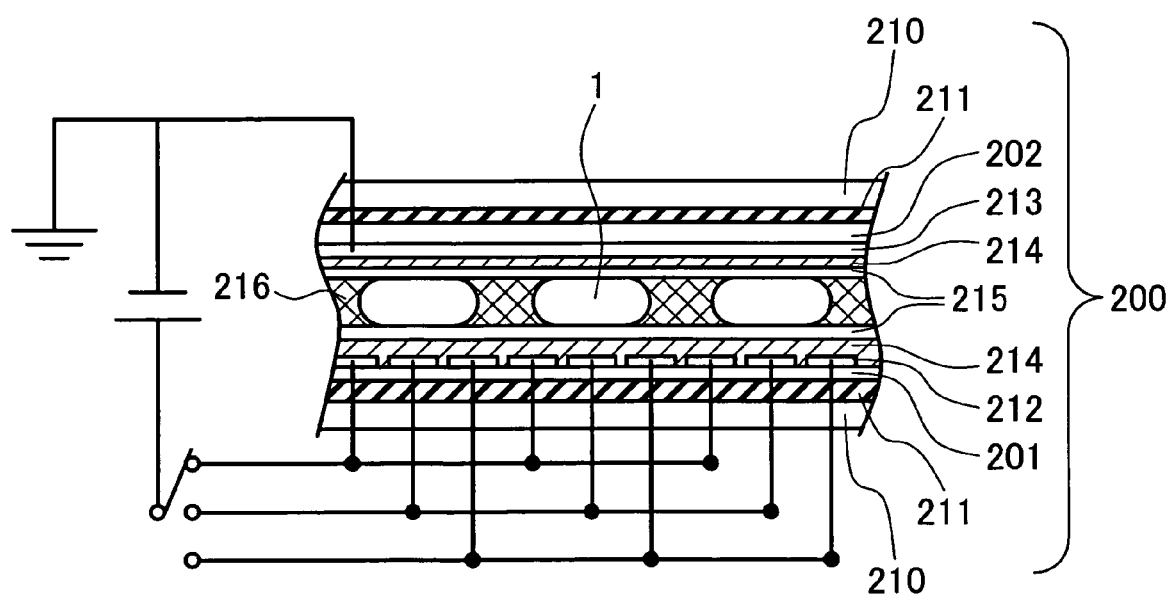
FIG. 6 shows a cross section of a fluid channel of the liquid transport substrate for the first embodiment of the present invention.

A cross-sectional view of the fluid channel 205 is shown in FIG. 6. In the first embodiment, a manner of transporting liquid droplets between two substrates is used. The transport substrate unit 200 is composed of a lower substrate 201, an upper substrate 202, thermal regulators (heaters) 211 which can regulate the temperatures of both substrates, and thermal insulations 210 as sheathing. In the first embodiment, the lower substrate 201 and the upper substrate 202 made of glass are employed; however, ceramic or silicon substrates may be used. In biochemical analysis, it is necessary keep the temperature of a reaction solution at 37° C. By the use of the thermal insulations 210, the temperature inside the substrates can be regulated precisely. By inserting a spacer or the like, a gap between both substrates is maintained constant. The fluid channel 205 is formed by arranging a plurality of lower electrodes 212 on the lower substrate 201. The top surfaces of the electrodes are covered by an insulation film so that electrolysis of the first liquid does not take place when voltage is applied to the electrodes. On the whole surface of the upper substrate 202, an upper electrode (layer) 213 connected to ground is laid with its bottom covered by an insulation film 214, like the tops of the lower electrodes 212. The plurality of lower electrodes 212 and the upper electrode layer are placed opposing each other. The top surfaces of the lower electrodes and the bottom surface of the upper electrode may be approximately parallel, that is, parallel within a tolerance, or separated by a given distance therebetween.

Between the upper electrode 213 and the lower electrodes 212, a positive voltage can be applied to the lower electrodes 212. The lower electrodes 212 and the upper electrode 213 are made of Indium Tin Oxide (ITO); however, they may be made of metal such as Cr and Al or silicon. As the insulation films 214, $SiO_2$ films are employed; instead, the following may be used: metal oxide films and metal nitride films such as Parylene, SiN, and tantalum oxide, fluorine water-repellent films such as TefonAF from DuPont and CYTOP from Asahi Glass Co. Ltd., silicon water-repellent films, and plasma-deposited fluorocarbon films. The innermost surfaces of both substrates are coated by water-repellent films 215. As the water-repellent films, TefonAF from DuPont is employed; instead, fluorine water-repellent films such as CYTOP from Asahi Glass, silicon water-repellent films, and plasma-deposited fluorocarbon films may be used. In the first embodiment, as interstitial material 216 filling the space between the substrates, silicon oil as a second liquid is employed; instead, fluorocarbon oil and paraffin oil may be used, or gas such as air may be used instead of the liquid. If fluorocarbon oil is used as the interstitial material 216, the specific gravity of fluorocarbon is as large as about 1.8 g/cm³ and, consequently, for a water-soluble sample with specific gravity of about 1.0 g/cm³, its buoyant force will make it hard to come in contact with the lower substrate.

If the first liquid droplet does not contact with the substrate, change in the wetting behavior of the droplet on the substrate is small and the droplet cannot be transported easily. In such a case, a plurality of electrodes may be arranged on the bottom of the upper substrate 202 to form a fluid channel 205. Wiring lines are routed to the lower electrodes 212, as shown in FIG. 6, so that a same voltage can be applied to one of every three electrodes, that is, synchronous voltage application occurs two electrodes apart and accordingly, sample droplets are advanced in steps of two electrodes apart. This is because, when sample droplets are moved to every other electrode, one droplet to be transported moves to touch the preceding droplet staying on an electrode to which a voltage is applied, and both droplets are mixed. Thus, it is needed to advance sample droplets in steps of two or more electrodes apart. Voltage to be applied two or more electrodes apart to advance sample droplets in this way can be controlled under a same line at least every three electrodes. Because the number of control switches decreases, control of transporting sample droplets becomes easy accordingly.

Figure 7:
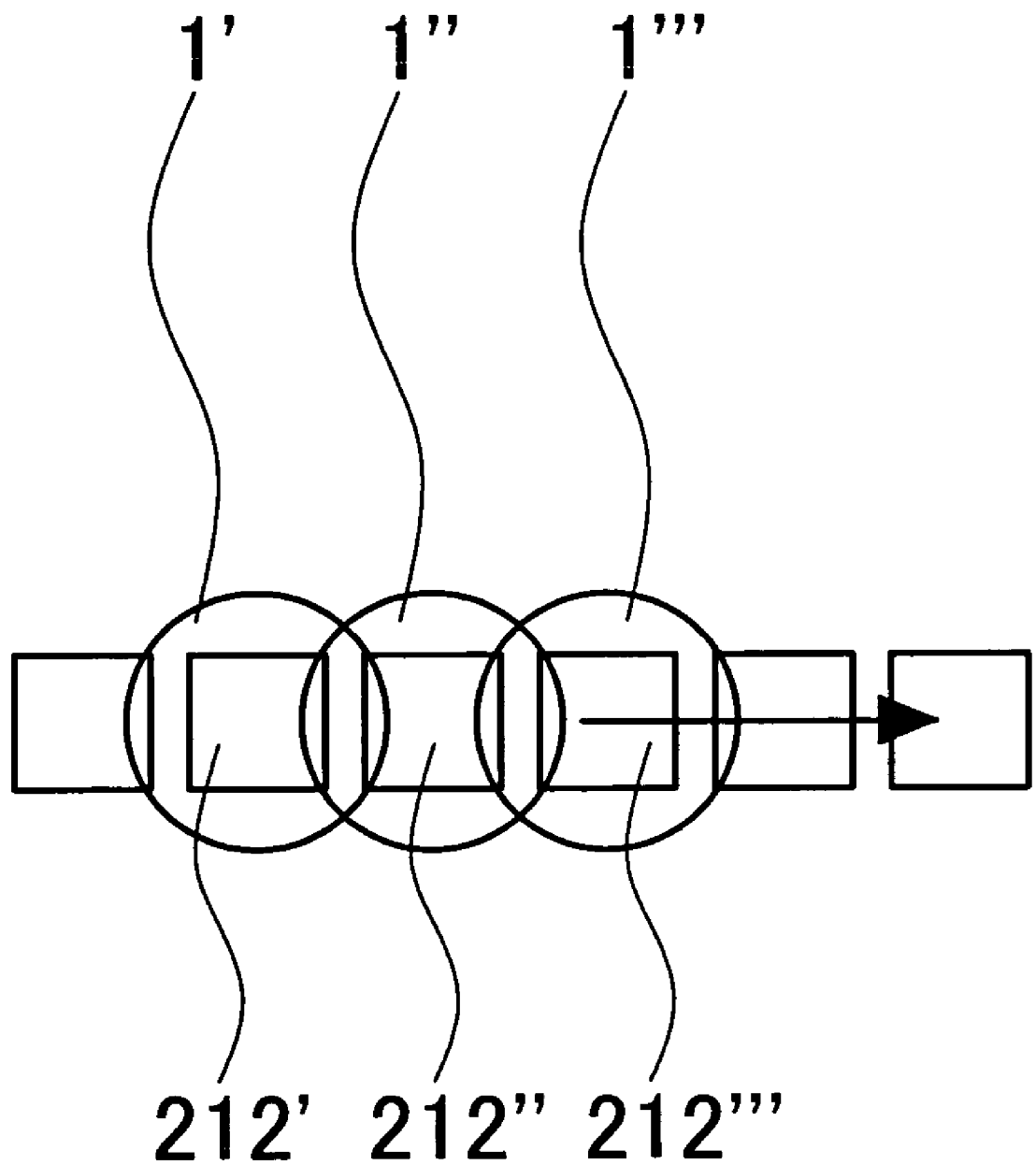
FIG. 7 explains the liquid transport manner for the first embodiment of the present invention.

As described above, the fluid channel 205 is formed by the plurality of lower electrodes 212. By using FIG. 7, the arrangement of the lower electrodes 212 and the liquid transport manner are explained. First, voltage is applied to a lower electrode 212' and a sample droplet 1' moves to above the lower electrode 212'. When the voltage application to the lower electrode 212' is turned off, this electrode 212' is placed in an electrical floating state, not connecting to ground, and other electrodes are electrically floating. To transport the sample droplet 1' staying on the lower electrode 212' from the left to the right direction in FIG. 7, voltage is applied to a lower electrode 212" with the lower electrode 212' being electrically floating. Then, the sample droplet 1' moves to the position of the lower electrode 212", when it is positioned as a sample droplet 1" depicted. Next, after the potential of the lower electrode 212" is dropped to ground, with the lower electrode 212" being electrically floating, voltage is applied to a lower electrode 212'". Then, the sample droplet 1" moves to the position of the lower electrode 212'", when it is positioned as a sample droplet 1'" depicted. By repeating the above, the sample droplet 1' can be transported from the left to the right direction.

Figure 8:
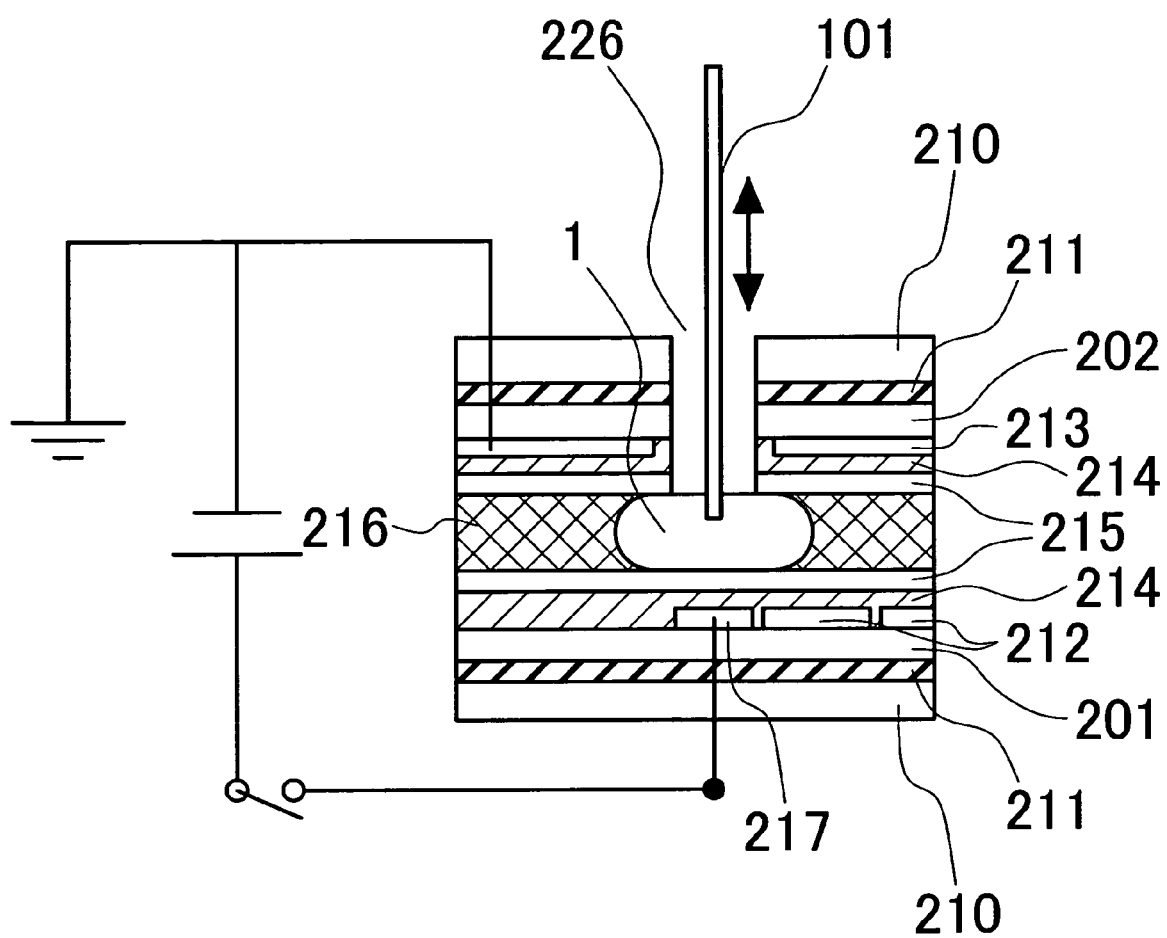
FIG. 8 shows a detailed view of a sample inlet for the first embodiment of the present invention.

A cross-sectional view of the sample inlet 203 is shown in FIG. 8. A sample inlet hole 226 is provided through the upper substrate 202 and, through the sample inlet hole 226, the pipetter 101 drops and dispenses a sample droplet 1 into the interstitial material 216 above an electrode 217 at the sample inlet on the inside of the lower substrate 201. When the pipetter 101 is withdrawn from the sample inlet hole 226, the upper electrode 213 is connected to ground and voltage is applied to the electrode 217 at the sample inlet, which effects a good wetting behavior of the sample droplet 1 on the lower substrate 201 and upper substrate 202 by electrocapillarity. Thereby, the dropped sample droplet 1 can be transferred into the transport substrate unit 200 without adhering to the pipetter 101. After dispensed into the interstitial material, the sample droplet 1 is transported through the fluid channel 205 by applying voltage between a lower electrode 212 next to the electrode 217 at the inlet and the upper electrode 213.

Figure 9:
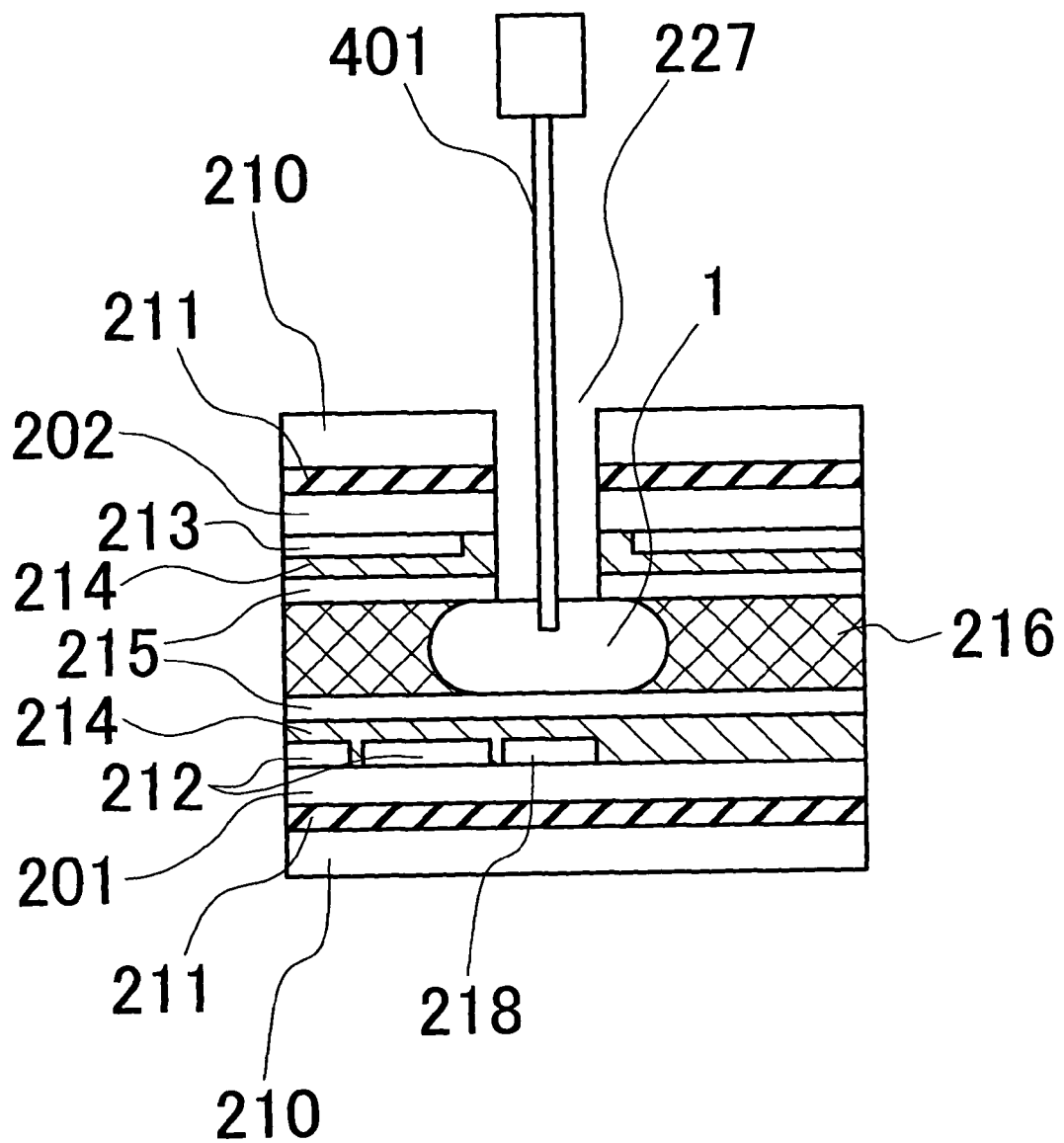
FIG. 9 shows a detailed view of an outlet for the first embodiment of the present invention.
Figure 10:
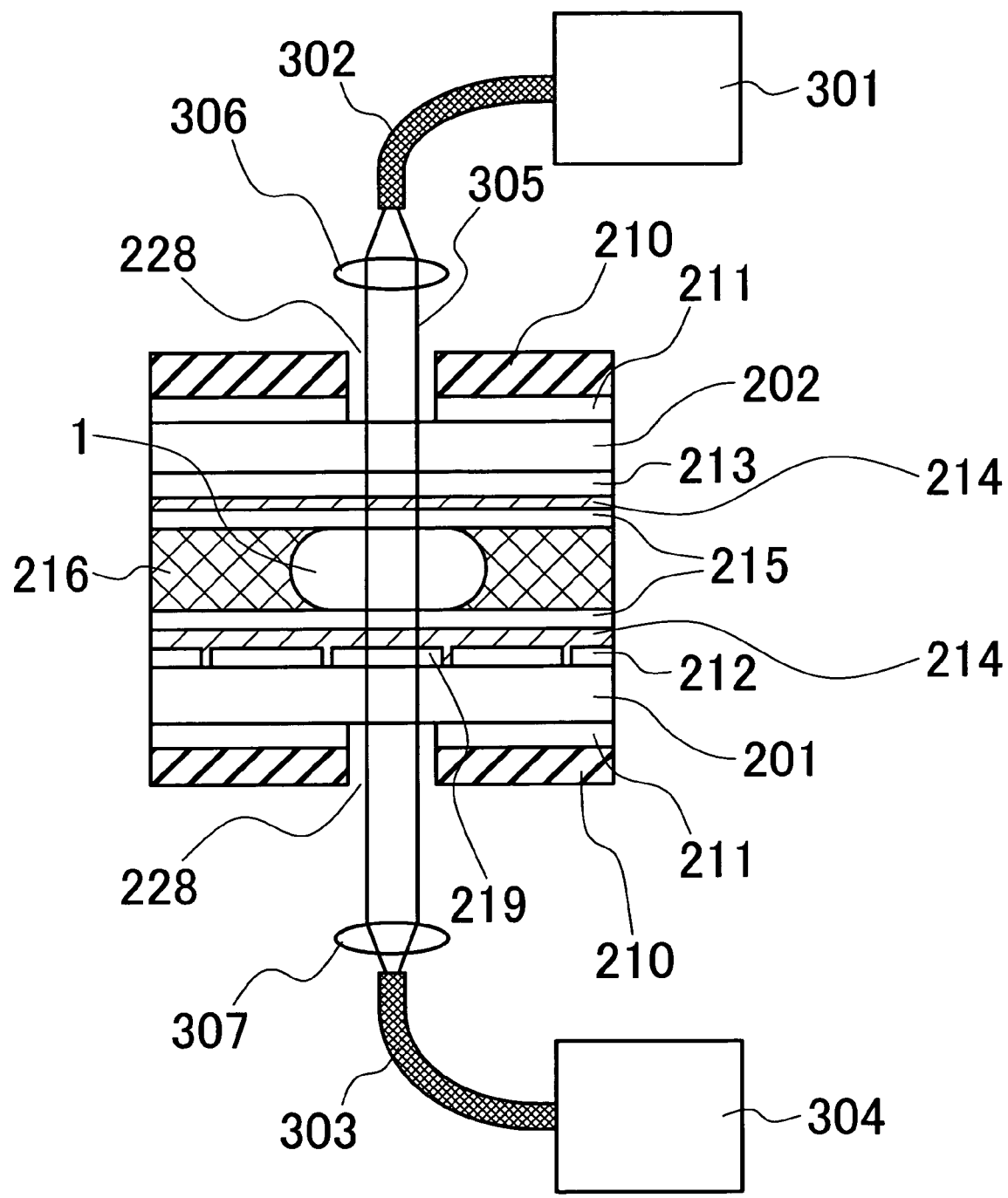
FIG. 10 shows a detailed view of a measuring section for the first embodiment of the present invention.

A cross-sectional view of the outlet 204 is shown in FIG. 9. An outlet hole 227 is provided through the upper substrate 202 and a sample droplet 1 transported through the fluid channel 205 to the outlet 204 is drawn by the shipper 401 above an electrode 218 at the outlet, transferred to the ejection tank 402, and merged into other sample droplets 1. FIG. 10 shows the construction of the optics unit 300 and a vertical cross-sectional view of the measuring section 206 inside the transport substrate unit 200. Within the optics unit 300, a sensing assembly consisting of a light source 301, an irradiating light fiber 302, a light-collecting fiber 303, a measuring instrument 304, an irradiation lens 306, and a collective lens 307 is installed. In the measuring section 206, openings are formed as penetration windows 228 in the insulations 210 and heaters 211 of both the upper and lower substrates so that light can pass through the substrates. Light 305 emitted from the light source 301 passes through the irradiating light fiber 302 and the irradiation lens 306 and hits the bottom of one penetration hole 208. The light struck on the upper substrate passes through the upper substrate 202 and its insulation film 214 and water-repellent film 215, passes through a sample droplet 1 staying above an electrode 219 in the measuring section, and passes through the lower water-repellent film 215 and insulation film 214, the electrode 219 in the measuring section, and the lower substrate 201. The light going out of the other penetration hole 228 of the lower substrate is collected by the collective lens 307 and sent through the light-collecting fiber 303 to the measuring instrument 304. The light entering the measuring instrument 304 is dispersed by grating and received by photodiodes for each wavelength component.

While sample droplets 1 which were subjected to measurement are drawn one by one by the shipper 401, a sample droplet subjected to measurement may be merged into other droplets within the substrate and then drawn by the sipper 401. While serum is analyzed as is without being diluted in this embodiment, it is possible to dilute serum with water in the sample disk unit. While serum is used as a sample liquid in this embodiment, water and other liquids may be used as a sample liquid and the present invention can be applied to turbidity measurements thereof. While the manner in which liquid droplets are sandwiched between two substrates is used in this embodiment, instead of the opposing substrates, wires may be used, as described, e.g., in [patent document 4] or liquid droplets may be transported on a single substrate, as described, e.g., in [patent document 5] in order to simplify a practical device manufacturing process. In such cases, because access to liquid droplets being transported from above is easy, an electrode with its surface covered by an ion-selective film (e.g., non-patent document 3) may be provided in the measuring section and the amounts of ions as components of a sample droplet may be measured.

A second embodiment will be described below. In the second embodiment, serum is used as a sample liquid and a plurality of sample droplets are serially transported substantially in one direction on a substrate. A sample droplet is mixed with a reagent, the intensity of light transmitted through a mixture is measured in the measuring section, and lactate dehydrogenase measurement is performed.

Figure 11:
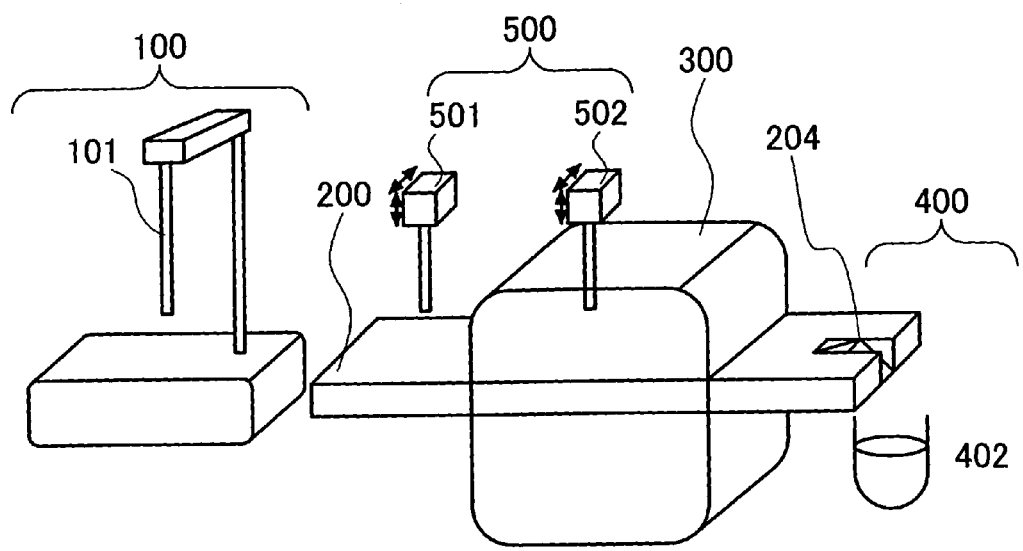
FIG. 11 is a schematic showing apparatus setup for a second embodiment of the present invention.

Apparatus setup is shown in FIG. 11. The apparatus is composed of a sample disk unit 100, a transport substrate unit 200, an optics unit 300, an ejection unit 400, and a reagent supply unit 500. The reagent supply unit 500 consists of a first reagent dispenser 501 and a second reagent dispenser 502. Reagents dropped out of these dispensers are mixed with a sample droplet at different timing. A first reagent is contained in a reagent reservoir installed in or connected to the first reagent dispenser 501 and a second reagent is contained in a reagent reservoir installed in or connected to the second reagent dispenser 502.

As is the case for the first embodiment, a sample droplet is dispensed from the sample disk unit 100 into the transport substrate unit 200 by the pipetter 101. After the sample droplet is mixed with a first reagent as a third liquid dropped out of the first reagent dispenser 501, measurement is made on a mixture. After it is further mixed with a second reagent dropped out of the second reagent dispenser 502, measurement is made on a mixture again. The sample droplet which was subjected to the measurements is eventually ejected from the outlet 204 to the ejection tank 402 within the ejection unit 400.

The construction of the sample disk unit 100 is the same as that for the first embodiment. As the reagents, Pureauto S LD from Daiichi Pure Chemical Co., Ltd. is used.

Figure 12:
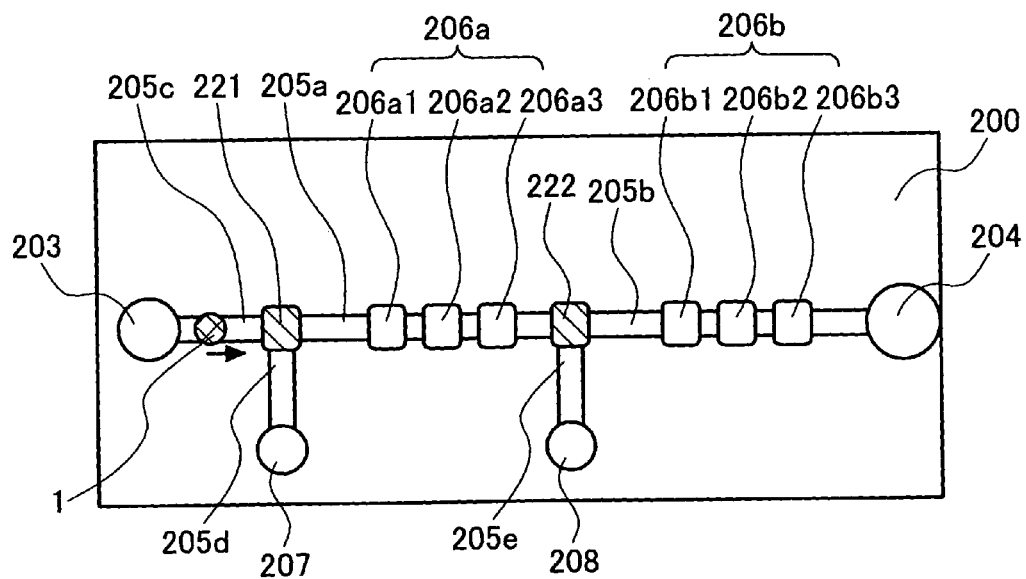
FIG. 12 shows a layout of the elements of the liquid transport substrate for the second embodiment of the present invention.

A layout of the elements inside the transport substrate unit 200 is shown in FIG. 12. The transport substrate unit 200 is composed of a sample inlet 203, a first reagent inlet 207, a second reagent inlet 208, a first reagent mixing section 221, a second reagent mixing section 222, three first measuring sections 206a, three second measuring sections 206b, and an outlet 204. The sample inlet 203 and the first reagent mixing section 221 are connected by a fluid channel segment 205c, the first reagent inlet 207 and the first reagent mixing section 221 are connected by a fluid channel segment 205d, the first reagent mixing section 221 and the second reagent mixing section 222 are connected by a fluid channel segment 205a, the second reagent inlet 221 and the second reagent mixing section 222 are connected by a fluid channel segment 205e, and the second reagent mixing section 222 and the outlet 204 are connected by a fluid channel segment 205b.

A sample droplet 1 as the first liquid dispensed into the sample inlet 203 by the pipetter 101 passes through the fluid channel segment 205c and is transported to the first reagent mixing section 221. A first reagent 503 dropped into the first reagent inlet 207 from the first reagent dispenser 501 passes through the fluid channel segment 205d and is transported to the first reagent mixing section 221. In the first reagent mixing section 221, the sample droplet 1 and the first reagent 503 are mixed and a first reaction solution 2 is prepared. While the first reaction solution 2 passes through the fluid channel segment 205c and is transported to the second reagent mixing section 222, it is measured during passage through the three first measurement sections 206a. A second reagent 504 dropped into the second reagent inlet 208 from the second reagent dispenser 502 passes through the fluid channel segment 205e and is transported to the second reagent mixing section 222. In the second reagent mixing section 222, the first reaction solution 2 and the second reagent 504 are mixed and a second reaction solution 3 is prepared. While the second reaction solution 3 passes through the fluid channel segment 205b and is transported to the outlet 204, it is measured during passage through the three second measurement sections 206b. Eventually, the second reaction solution 3 is ejected from the outlet 204 to the ejection tank 402 outside of the transport substrate unit 200, as shown in FIG. 11.

The constructions of the sample inlet 203 and the fluid channel 205 are the same as described for the first embodiment. The constructions of the first reagent inlet 207 and the second reagent inlet 208 are the same as the construction of the sample inlet 203 described for the first embodiment, except that, instead of the pipetter 101, the first reagent dispenser 501 is connected to the first reagent inlet 207 and the second reagent dispenser 502 is connected to the second reagent inlet 208. The construction of the fluid channel 205 is the same as described for the first embodiment.

Figure 13:
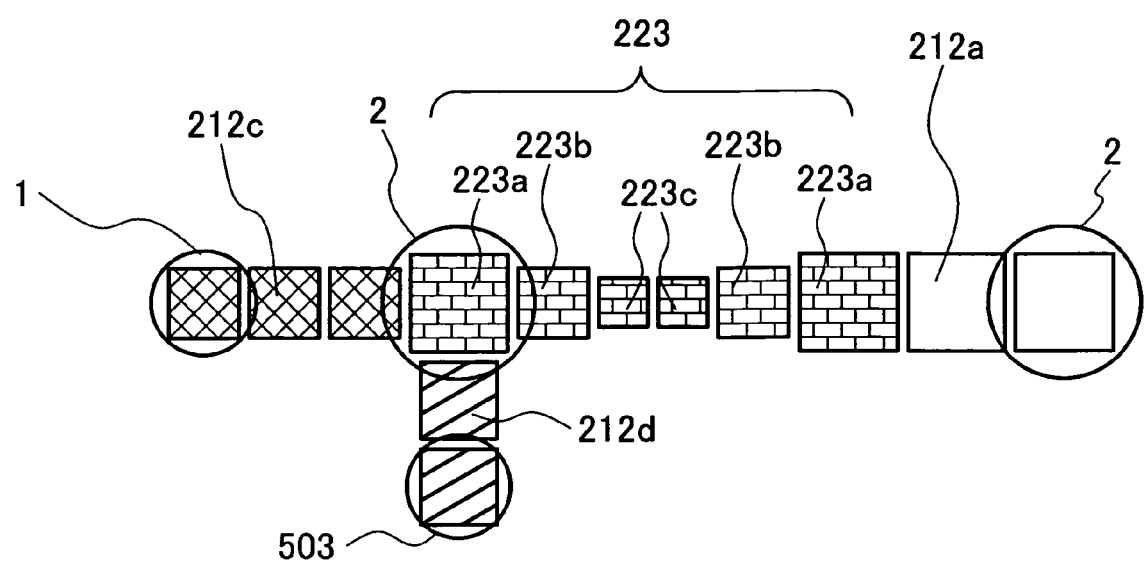
FIG. 13 shows a detailed view of one mixing section for the second embodiment of the present invention.

A pattern of lower electrodes 212 in the first reagent mixing section 221 is shown in FIG. 13. A plurality of electrodes 223 in the first mixing section are arranged to mix a sample droplet 1 and a first reagent 503. In time with when a sample droplet 1 is transported to the first reagent mixing section 221, a first reagent 503 droplet is transported, and the sample and first reagent droplets are combined into a first reaction solution 2 droplet and mixed by making the solution droplet reciprocate a few times over the electrodes 223 for the first mixing section. Because a droplet of the first liquid becomes easier to transport when in contact with a plurality of electrodes, the electrodes are dimensioned, according to the size of the droplet to be transported by each electrode. Since a gap between two substrates is 0.5 mm in this embodiment, on the assumption that a columnar droplet lies between the substrates, the contact area between a 10-microliter droplet and either substrate becomes a circle with a radius of about 2.5 mm. If electrodes are of a 3.5 mm by 3.5 mm square and a gap between neighboring electrodes is 100 μm, a droplet of the above volume can be brought in contact with a plurality of electrodes. Since the volume of a sample droplet is 1 microliter and the volume of a first reagent droplet is 10 microliters in this embodiment, lower electrodes 212c for transporting a sample droplet are dimensioned to a size of 1 mm square, lower electrodes 212d for transporting a first reagent 503 droplet are dimensioned to a size of 3.5 mm square, and lower electrodes 212a for transporting a first reaction solution 2 droplet are dimensioned to a size of 3.7 mm square. That is, the volume of a sample droplet is smaller than the volume of a reagent droplet or reaction solution droplet and, accordingly, the size of the electrodes for transporting a sample droplet is made smaller than the size of electrodes for transporting a reagent or reaction solution.

Figure 14:
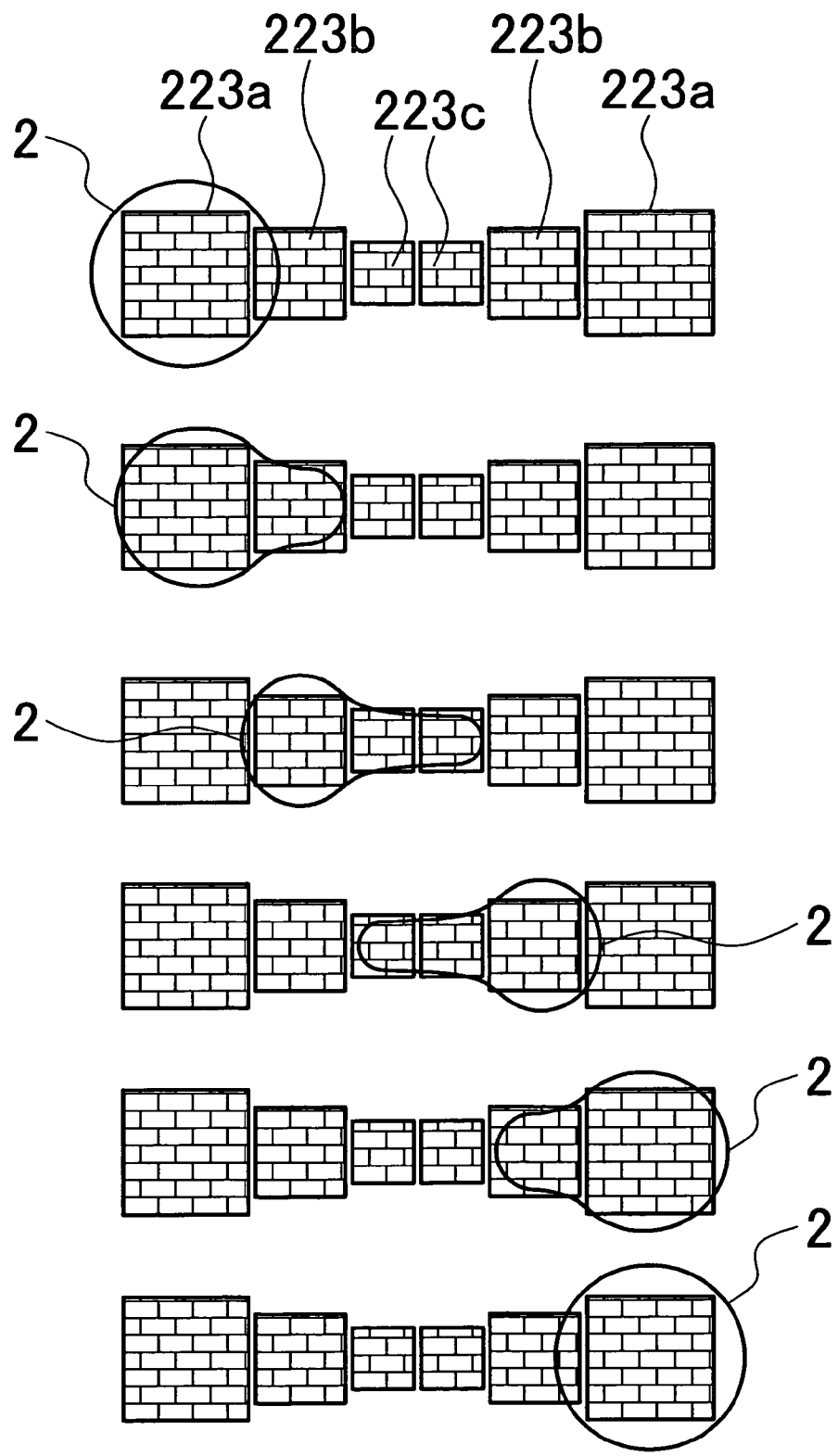
FIG. 14 shows detailed views of the one mixing section for the second embodiment of the present invention.

The electrodes in the first mixing section are divided into electrodes 223a with a size of 2.9 mm square, electrodes 223b with a size of 2.0 mm square, and electrodes 223c with a size of 1.5 mm square. That is, the electrodes at either ends of the mixing section are greatest, the electrodes adjacent to the end electrodes in the mixing section are of medium size, and the electrodes in the middle of the mixing section are smallest. When a droplet of the first reaction solution 2 moves over the electrodes having different sizes, its shape changes, according to the size of a electrode above which it is moving and the solution is mixed well, as is illustrated in FIG. 14.

Figure 15:
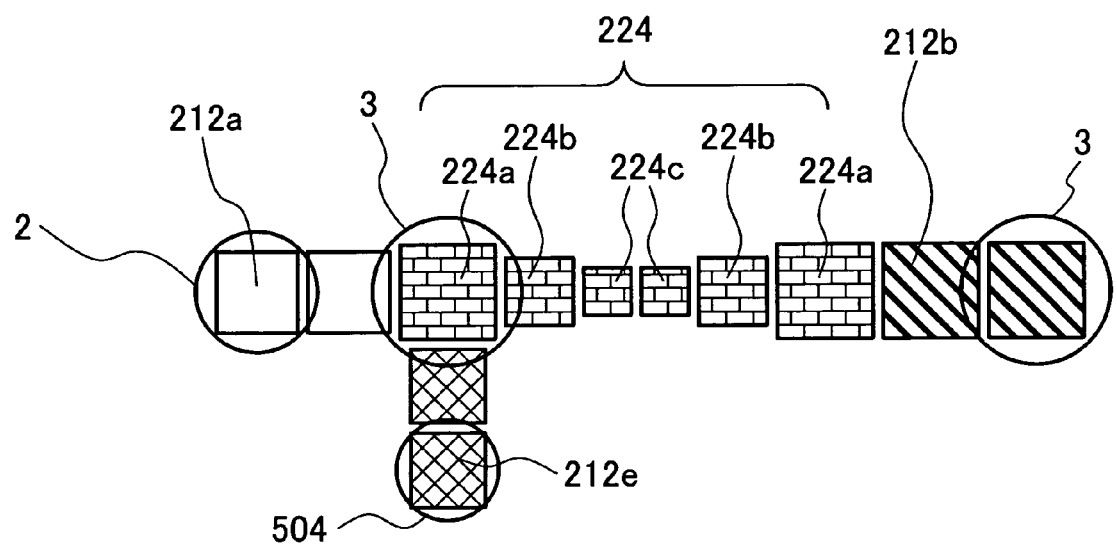
FIG. 15 shows a detailed view of another mixing section for the second embodiment of the present invention.

A pattern of lower electrodes 212 in the second reagent mixing section 222 is shown in FIG. 15. Similarly to the first reagent mixing section 221, a plurality of electrodes 224 in the second mixing section are arranged to mix a first reaction solution 2 and a second reagent 504 and a second reaction solution 3 is mixed by making its droplet reciprocate a few times over the electrodes 224 in the second mixing section. The electrodes are dimensioned, according to the size of the droplet to be transported by each electrode to make transport easy. In this embodiment, the volume of a second agent 504 droplet is 5 microliters, and lower electrodes 212e for transporting that droplet are dimensioned to a size of 2.5 mm square, whereas lower electrodes 212b for transporting a second reaction solution 3 droplet are dimensioned to a size of 4.5 mm square. That is, the size of the electrodes for transporting a sample droplet is made smaller than the size of electrodes for transporting a reaction solution.

Figure 16:
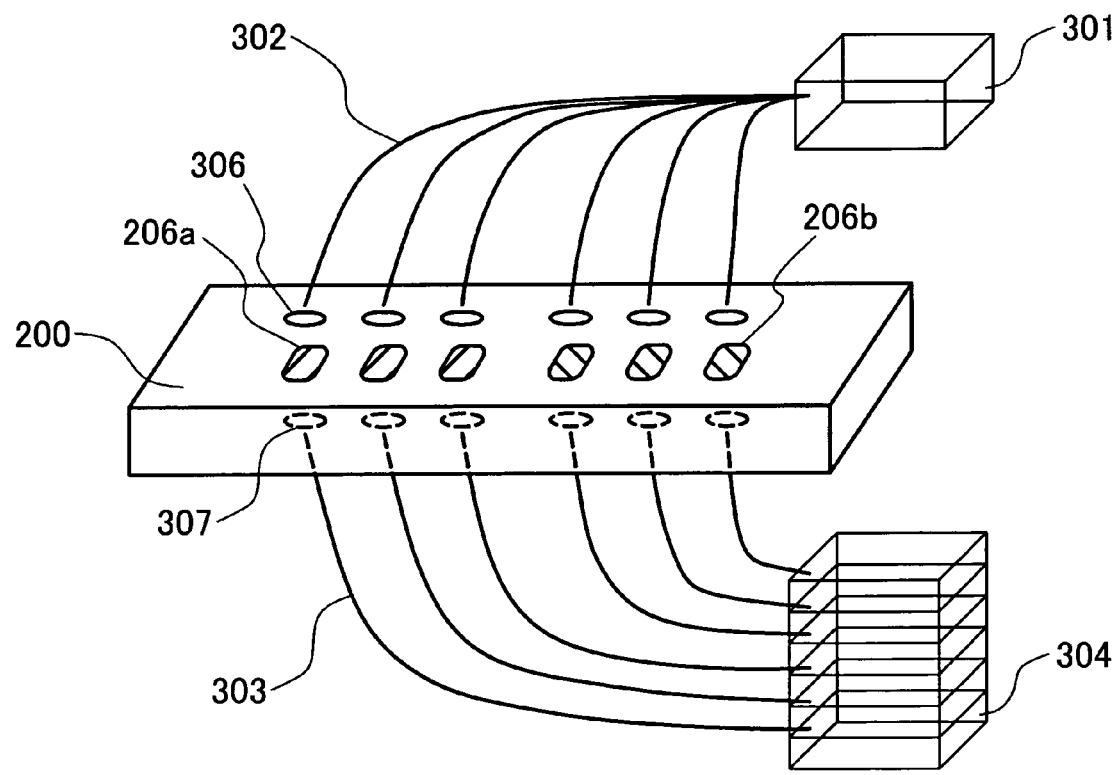
FIG. 16 shows a layout of a portion of the liquid transport substrate and an optics unit for the second embodiment of the present invention.

The construction of the optics unit 300 is shown in FIG. 16. The optics unit 300 is composed of a light source 301, six irradiating light fibers 302, six light-collecting fibers 303, a measuring instrument 304, six irradiation lenses 306, and six collective lenses 307. Light emitted from the light source 301 is divided by the irradiating light fibers 302 and routed to the measuring sections 206. By the irradiation lenses arranged so that light from each of the irradiating light fibers 302 is condensed efficiently to hit on each measuring section, the light hits on each measuring section 206. The light transmitted through each measuring section 206 is collected by each of the collective lenses 307 arranged so that the transmitted light 305 is condensed efficiently. The transmitted light 305 passes through each of the light-collecting fibers 303 and is guided to the corresponding section of the measuring instrument 304. In the measuring instrument 304, the light is dispersed by grating, the intensity of the transmitted light from each measuring section 206 is measured on a per-wavelength basis by photodiodes, and absorbance is obtained.

Figure 17:
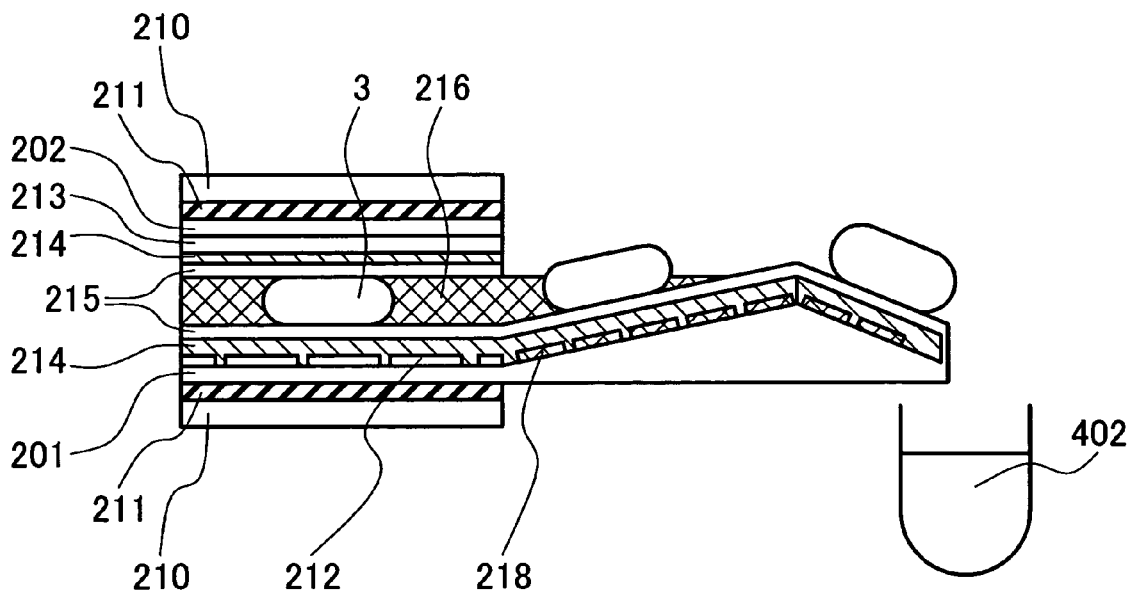
FIG. 17 shows a detailed view of an outlet for the second embodiment of the present invention.

A cross section of the outlet 204 is shown in FIG. 17. In the second embodiment, a great number of electrodes 218 in the outlet are installed to form ascending and descending slopes so that the interstitial material filling the internal does not leak out and only sample droplets are transported outside. After reaction solution droplets pass beyond the top of the slopes, they are transported electrically over the electrodes by the aid of gravity, eventually fall from the substrate by gravity, and are ejected into the ejection tank 402 installed beneath the outlet.

The procedure of measuring operation will be described. A calibration liquid is first measured as a sample 1 and, from the measurement results, errors among the plurality of measuring sections are corrected. Next, a lactate dehydrogenase calibrator is measured and assay doses are obtained, and then serum is measured. The temperature of the transport substrate unit 200 is regulated so that its whole temperature will remain constant. First, calibration liquid droplets as the sample 1 are drawn by the pipetter 101 and dispensed into the sample inlet 203 inside the transport substrate unit 200. Next, lactate dehydrogenase calibrator and serum droplets are dispensed. Each sample droplet dispensed is serially fed from the sample inlet 203 into the fluid channel 205 and transported to the first reagent mixing section 221. At the same time, a first reagent is dispensed from the first reagent dispenser 501 into the first reagent inlet 207 inside the transport substrate unit 200 and a second reagent is dispensed from the second reagent dispenser 502 into the second reagent inlet 208. Then, a sample droplet 1 is mixed with a first reagent 503 droplet in the first reagent mixing section 221 and a resulting first reaction solution 2 droplet is transported to the second reagent mixing section 222, during which the intensity of light transmitted through the first reaction solution 2 is measured during passage through the first measuring sections 206a. About five minutes after the preparation of the first reaction solution 2 by mixing the sample droplet 1 and the first reagent 503, a droplet of the first reaction solution 2 is mixed with a second reagent 504 droplet in the second reagent mixing section 222 and a resulting second reaction solution 3 droplet is transported to the outlet 204, during which the intensity of light transmitted through the second reaction solution 3 is measured during passage through the second measuring sections 206b. In the second embodiment, the first measuring sections and the second measuring sections are configured with a plurality of electrodes corresponding to each section. However, when appropriate for the object to be measured, it is possible to provide either the first measuring sections or the second measuring sections only and it is also possible to provide first and second single-electrode measuring sections.

In the second embodiment, lactate dehydrogenase is a substance that is assayed and two reagents, the first and second reagents, are mixed with a sample to assay this substance. Thus, two mixing sections are provided in this embodiment. Reaction solution droplets which are subjected to the measurements are serially ejected to the ejection tank. The above operation is performed serially for all sample droplets dispensed from the sample disk unit 100.

In this embodiment, by carrying out mixing with the reagents and transports serially, amounts of lactate dehydrogenase as the assay for biochemical analysis are measured. A sample droplet is inserted every 10 seconds and it takes one minute for the droplet to arrive at the first measuring section 206, 10 minutes for the droplet to pass from the first measuring section 206 to the last measuring section 206, and one minute for the droplet to pass from the last measuring section 206 to the outlet 204. It takes a total of 12 minutes to complete the analytic process for one sample droplet. However, by sequentially manipulating sample droplets, time required for the analysis of 40 sample droplets is about 18.6 minutes (40 droplets×10 sec+12 min=400 sec+12 min≈18.6 min). As above, in this embodiment, by continuous operation of serial analysis processing, it is possible to complete measuring a large number of droplets in a short time.

Also in the second embodiment, based on absorbance change with time for five minutes after mixing a sample with the second reagent, the amount of the lactate dehydrogenase ingredient is calculated. The more the number of times of absorbance measurement made regularly during the five minutes, the more accurate measurement can be obtained. Absorbance change with time after mixing a sample with the first reagent is important for checking the effect of substances other than lactate dehydrogenase. Thus, three measuring sections are provided after the mixing with the first reagent and three measuring sections are provided after the mixing with the second reagent. Specifically, measuring sections 206a1, 206a2, and 206a3 as the first measuring sections 206a and measuring sections 206b1, 206b2, and 206b3 as the second measuring sections 206b are provided. The measuring sections measure absorbance of light at 340 nm in reference to the intensity of transmitted light at a wavelength of 405 nm. If the measurement is performed by one measuring section, sample droplets are transported through the section at intervals of 10 seconds. Therefore, absorbance change with time for a maximum of 10 seconds can only be measured with one measuring section and accurate ingredient amount measurements cannot be obtained. If the measurement with the same measuring section is continued for five seconds, throughput decreases. As in the second embodiment, by measuring absorbance change of a reaction solution over time with a plurality of measuring sections at different timing, accurate ingredient amount measurements can be obtained at high throughput. By correcting measurement errors among these measuring by the calibrator, more accurate measurements can be performed.

Figure 18:
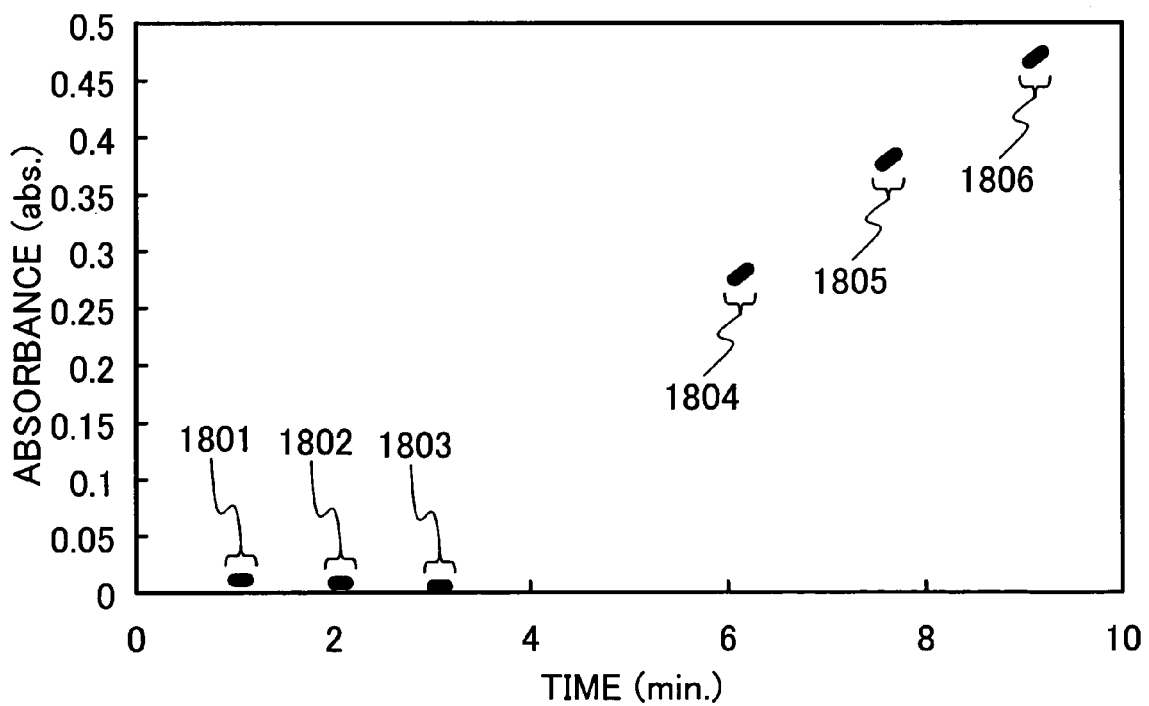
FIG. 18 shows measurement results for the second embodiment of the present invention.
Figure 19:
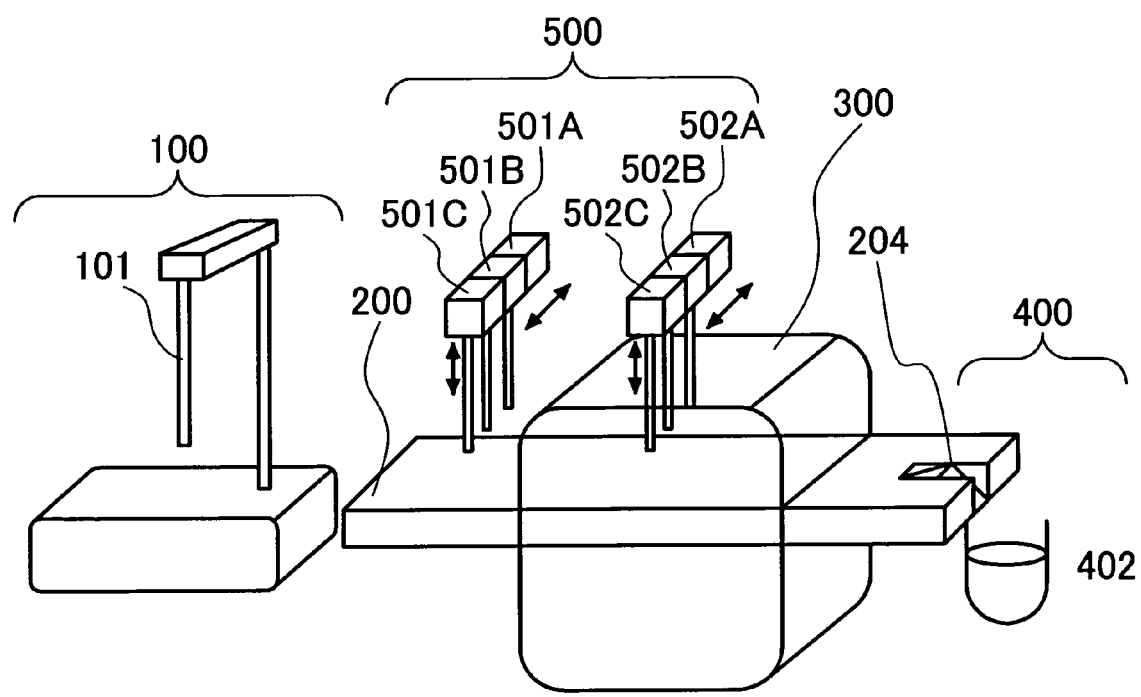
FIG. 19 is a schematic showing apparatus setup for a third embodiment of the present invention.

The results of measurements performed by the measuring sections 206a1, 206a2, 206a3, 206b1, 206b2, and 206b3 according to the second embodiment are shown all together in FIG. 18. Absorbance (abs.) is plotted on the ordinate and time (min.) after the mixing with the first reagent is plotted on the abscissa. The measuring section 206a1 made an absorbance measurement one minute after the mixing with the first reagent. The measuring section 206a2 made an absorbance measurement two minutes after the mixing with the first reagent. The measuring section 206a3 made an absorbance measurement three minutes after the mixing with the first reagent. The measuring section 206b1 made an absorbance measurement after six minutes after the mixing with the first reagent (one minute after the mixing with the second reagent). The measuring section 206b2 made an absorbance measurement after 7.5 minutes after the mixing with the first reagent (2.5 minutes after the mixing with the second reagent). The measuring section 206b3 made an absorbance measurement after nine minutes after the mixing with the first reagent (four minutes after the mixing with the second reagent). The results of the measurements made by the measuring sections 206a1, 206a2, 206a3, 206b1, 206b2, and 206b3 are plotted by points 1801, 1802, 1803, 1804, 1805, and 1806, respectively. It was assumed that one measuring section continues to take a measurement for 10 seconds. Change with time of the absorbance values measured by the measuring sections 206b1, 206b2, and 206b3 (a graph gradient in FIG. 18) is proportional to concentration. By checking against data of absorbance change with time for the calibrator, the concentration of lactate dehydrogenase in the sample droplet under this measurement was found to be 292.2 U/L. Like this, by measuring absorbance change with time, concentration can be measured. The more the number of measuring sections, the more data for the change with time can be obtained and the more accurate ingredient measurement can be performed.

A third embodiment will be described below. In the third embodiment, a plurality of fluid channels are provided, sample droplets are distributed from the sample inlet to these fluid channels, and throughput is improved by performing parallel measurements. Serum is used as a sample liquid, three fluid channels for measurements are provided, and substances, lipase, cholesterol, and C-reactive protein are assayed respectively along these fluid channels.

Apparatus setup is shown in FIG. 3. The apparatus is composed of a sample disk unit 100, a transport substrate unit 200, an optics unit 300, an ejection unit 400, and a reagent supply unit 500. The reagent supply unit 500 consists of first reagent dispensers 501A, 501B, and 501C and second reagent dispensers 502A, 502B, and 502C. A reagent, Liquitech Lipase Color from Rochu is used to assay lipase, a reagent, Pureauto S CHO-N from Daiichi Pure Chemical Co., Ltd. is used to assay cholesterol, and a reagent, Pureauto S CRP Latex from Daiichi Pure Chemical Co., Ltd. is used to assay C-reactive protein. For preparation, a first reagent to assay lipase is filled into a first reagent dispenser 501A and a second reagent to assay lipase is filled into a second reagent dispenser 502A. A first reagent to assay cholesterol is filled into a first reagent dispenser 501B and a second reagent to assay cholesterol is filled into a second reagent dispenser 502B. A first reagent to assay C-reactive protein is filled into a first reagent dispenser 501C and a second reagent to assay C-reactive protein is filled into a second reagent dispenser 502C.

A sample droplet is dispensed as a first liquid from the sample disk unit 100 into the transport substrate unit 200 by the pipetter 101. After the sample droplet is mixed with a first reagent 503 as a third liquid dropped out of a first reagent dispenser 501, measurement is made on a mixture. After it is further mixed with a second reagent 504 as a third liquid dropped out of the second reagent dispenser 502, measurement is made on a mixture again. The sample droplet which was subjected to the measurements is eventually ejected from the outlet 204 to the ejection tank 402 within the ejection unit 400.

Figure 20:
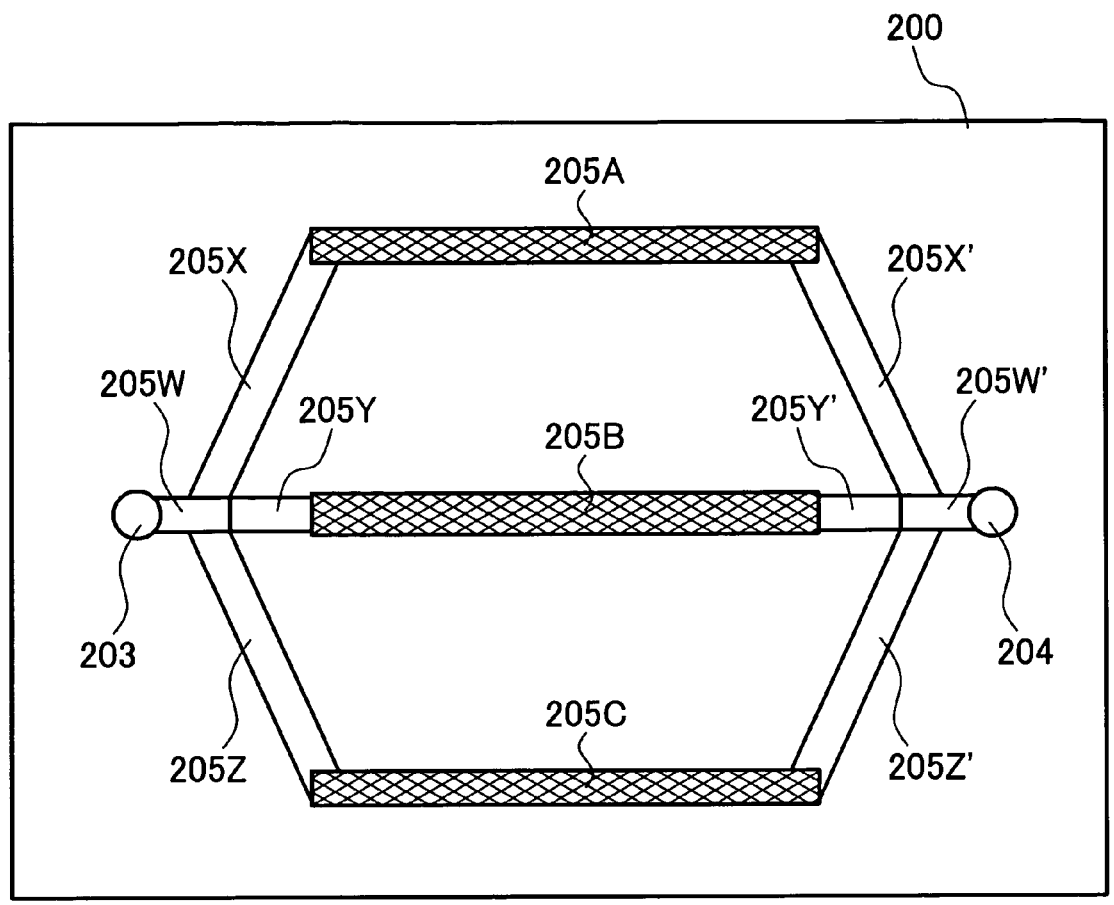
FIG. 20 shows a layout of fluid channels in the liquid transport substrate for the third embodiment of the present invention.

A layout of fluid channels 205 inside the transport substrate unit 200 is shown in FIG. 20. The sample inlet 203 and a plurality of fluid channels 205A, 205B, and 205C are connected by fluid diversion sections 205W, 205X, 205Y, and 205Z. The plurality of fluid channels 205A, 205B, and 205C and the outlet 204 are connected by fluid convergence sections 205W', 205X', 205Y', and 205Z'. While parallel fluid channels 205 are connected to one outlet 204 in this embodiment, each fluid channel 205 may be provided with an outlet 204 and sample droplets may be ejected outside the transport substrate unit 200. After a sample droplet is inserted from the sample inlet 203, it is distributed from a fluid diversion section 205W to any of the sections 205X, 205Y, and 205Z and transported. During the transport through each fluid channel 205, the sample droplet is measured. The droplet passes through any of the fluid convergence sections 205X', 205Y', and 205Z and a fluid convergence section 205W' and ejected from the outlet 204. Along a fluid channel 205A, lipase is assayed. Along a fluid channel 205B, cholesterol is assayed. Along a fluid channel 205C, C-reactive protein is assayed. Since three fluid channels are provided in this embodiment, throughput rises by a factor of about three as compared with a single fluid channel. If three substances are assayed with a single fluid channel, measurement sections for the three substances are arranged and, in this case, the number of measuring sections to assay each substance decreases, which may deteriorate measurement precision. In the third embodiment, the fluid channels are arranged separately for each substance to be assayed and, therefore, throughput rises and highly precise measurements can be performed.

Figure 21:
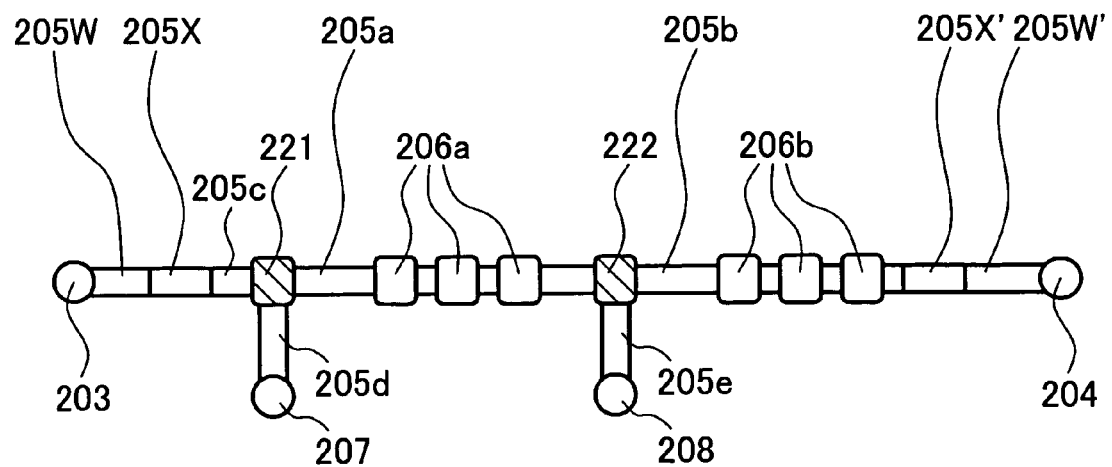
FIG. 21 shows a layout of the elements of the liquid transport substrate for the third embodiment of the present invention.

The configuration of the fluid channel 205A from the sample inlet 203 up to the outlet 204 is shown in FIG. 21. The fluid channels 205A, 205B, and 205C have basically the same configurations. In addition to the layout of the elements for the second embodiment, the sample inlet 203 is coupled via the fluid diversion sections 205W and 205W to one end of the fluid channel 205 and the other end of the fluid channel 205 is coupled via the fluid convergence sections 205W' and 205X' to the outlet 204. Along the fluid channel 205A, the first reagent dispenser 501A is connected to the first reagent inlet 207 and the second reagent dispenser 502A is connected to the second reagent inlet 208. Along the fluid channel 205B, the first reagent dispenser 501B is connected to the first reagent inlet 207 and the second reagent dispenser 502B is connected to the second reagent inlet 208. Along the fluid channel 205C, the first reagent dispenser 501C is connected to the first reagent inlet 207 and the second reagent dispenser 502C is connected to the second reagent inlet 208. To prevent measurement throughput from decreasing, the speed of transporting a sample droplet through the fluid diversion sections and through the fluid convergence sections is made different from the speed of transporting a sample droplet through each fluid channel; that is, the former speed is faster than the latter speed, specifically in this embodiment, three times faster than the latter speed.

Figure 22:
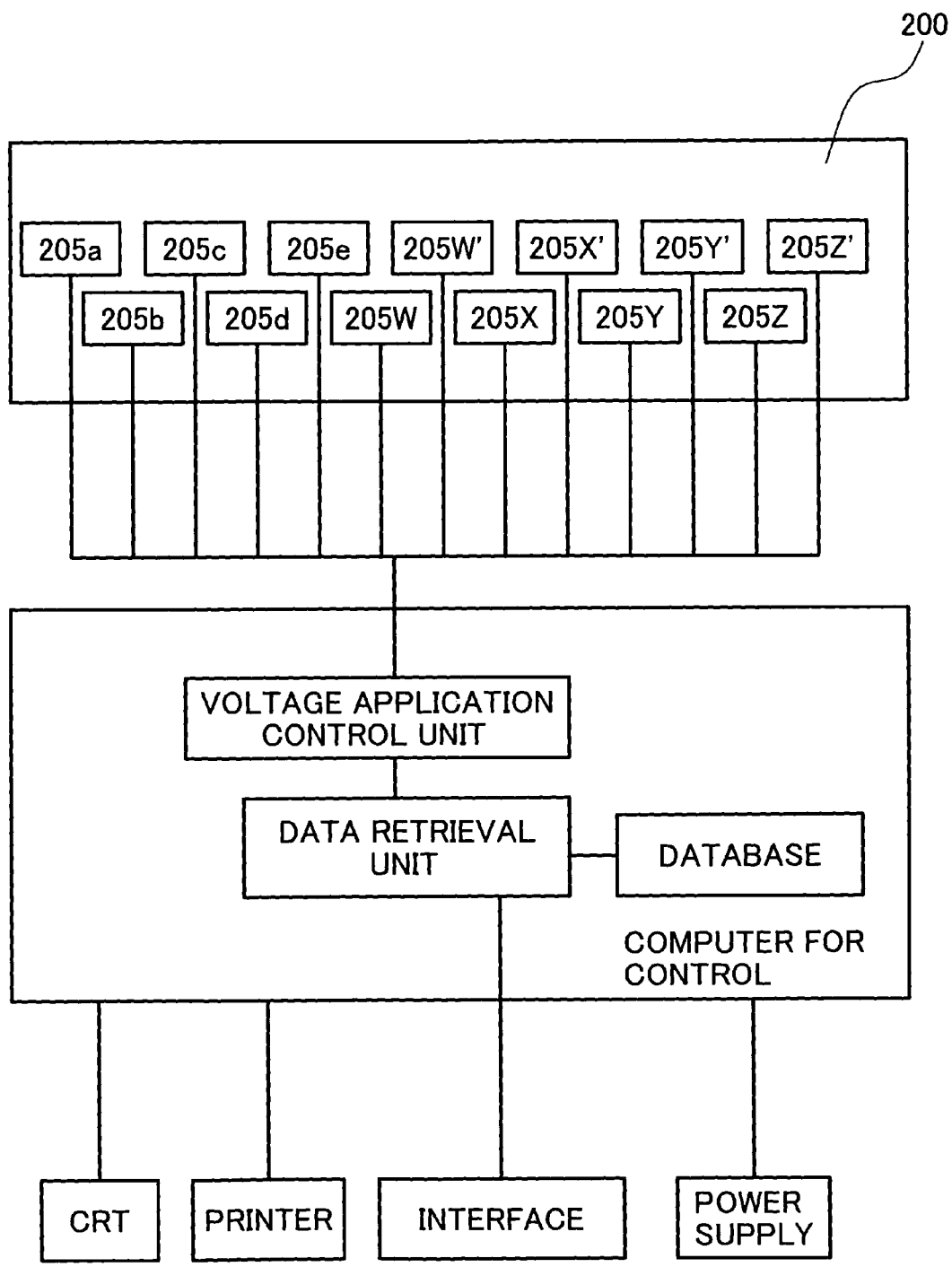
FIG. 22 shows an example of a configuration for control of lower electrodes for the third embodiment of the present invention.
Figure 23:
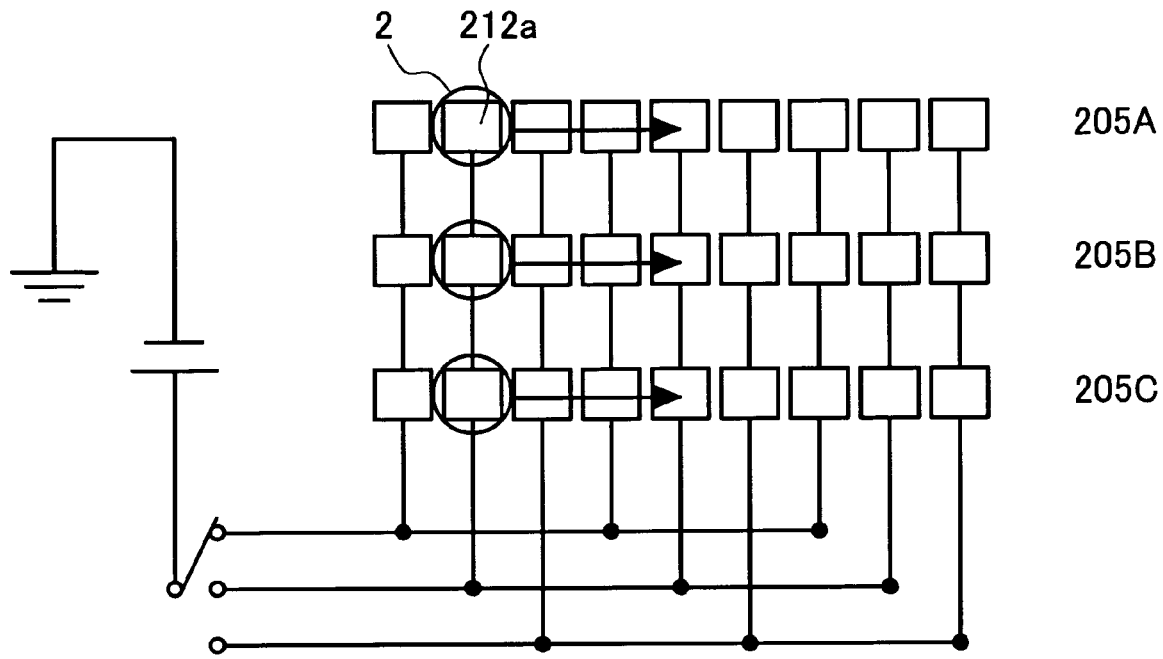
FIG. 23 shows the wiring arrangement for lower electrodes under the fluid channels in the liquid transport substrate for the third embodiment of the present invention.

A schematic of a control system is shown in FIG. 22. Control of voltage application to the segments of each fluid channel is performed by a computer for control independently. The computer for control is internally equipped with a data retrieval unit which, based on sample information entered via the interface, retrieves information corresponding to the sample information from the database, and a voltage application control unit which issues a command to apply a voltage to a fluid channel, according to an assay item included in the information corresponding to the sample information. Sample droplets are distributed to one of the fluid channels by the control of the voltage application control unit in accordance with an assay item which is obtained by referring to the database of registered assay items within the computer for control. Wiring arrangement for lower electrodes under a fluid channel segment 205a of each of the fluid channels 205A, 205B, and 205C is shown in FIG. 23. As is the case for the first embodiment, wiring lines are routed to the lower electrodes 212 within each fluid channel 205 so that a same voltage can be applied to one of every three electrodes, that is, synchronous voltage application occurs two electrodes apart and, accordingly, sample droplets are advanced in steps of two electrodes apart and transported. Moreover, these wiring lines extend to apply voltage to the electrodes in corresponding positions under all fluid channels so that synchronous transports occur. Even if the number of fluid channels becomes large, wiring to the electrodes for the fluid channels arranged in parallel can be controlled in an integrated fashion by a single switch and it becomes easy to control transports of sample droplets.

In the third embodiment, three fluid channels 205 are placed in parallel and one fluid channel consisting of five segments 205a, 205b, 205c, 205d, and 205e. For these fluid channels, 15 control entities (5×3=15) are usually required. However, by applying integrated control over the channels in corresponding segments, the required number of control entities is reduced to five and it is easy to control voltage application to the electrodes even for parallel fluid channels. While one substance is only assayed along one channel in this embodiment, another substance may be assayed along one channel by connecting another dispenser and supplying another reagent if the same wavelength is sensed. If it is necessary to repeat assaying a substance a great number of times, the same substance may be assayed along a plurality of fluid channels.

Figure 24:
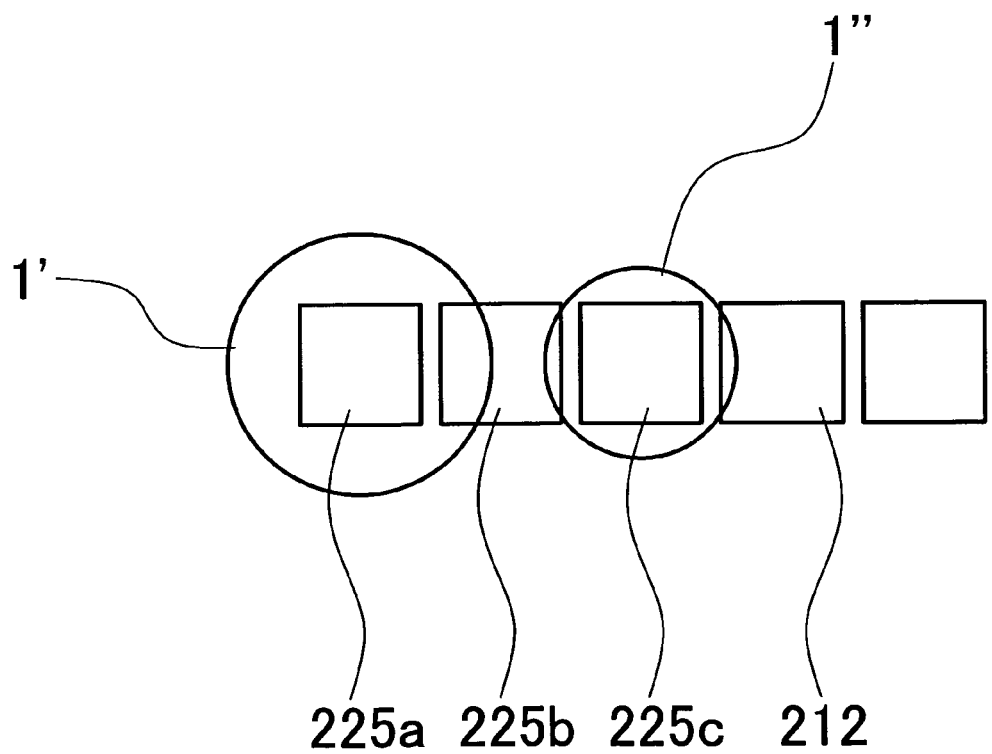
FIG. 24 explains a manner of inserting a sample droplet into the sample inlet in the liquid transport substrate for the third embodiment of the present invention.

A layout of electrodes 225 in the inlet and lower electrodes 212 on the lower substrate 201 in the sample inlet 203 is shown in FIG. 24. There are three electrodes 225a, 225b, and 225c in the inlet. First, a sample droplet 1' which is about three times as much as the required dose for measurement is dispensed by the pipetter 101 into the sample inlet 203 inside the transport substrate unit 200 and this droplet is placed above an electrode 225a in the inlet. In this state, when voltage is applied to electrodes 225b and 225c in the inlet, the sample droplet 1' extends over the electrodes 225b and 225c in the inlet. Then, voltage application to the electrode 225b in the inlet is turned off and, after the electrode is connected to ground, it is made electrically floating. When voltage is applied to the electrodes 225a and 225c in the inlet, the sample droplet 1' is split into two parts, one placed above the electrode 225a and the other placed above the electrode 225c. Next, voltage is applied to a lower electrode 212W under the fluid diversion section 205, a given dose of a sample droplet 1'' as a first liquid is transported through the fluid diversion section 205.

Figure 25:
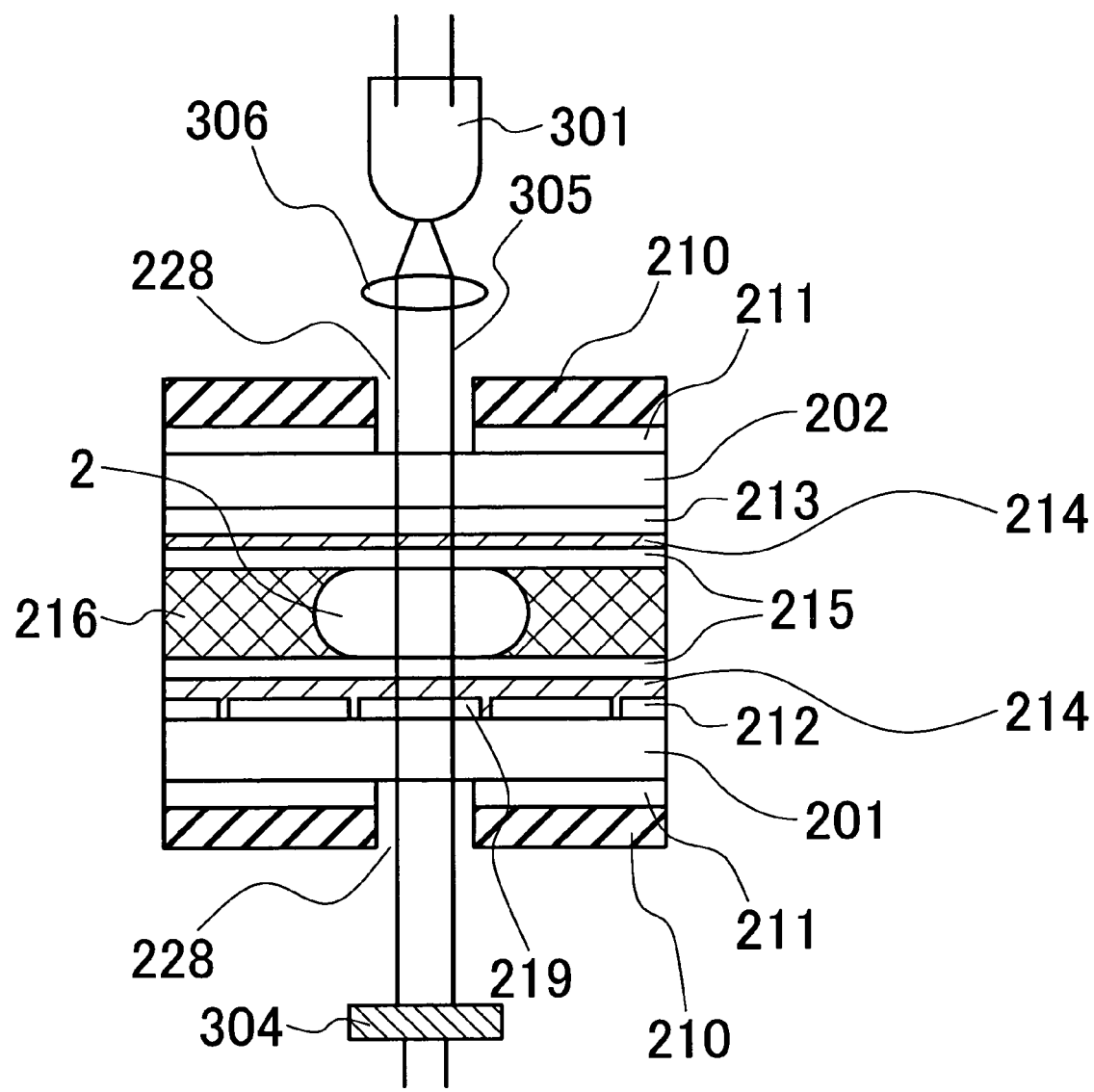
FIG. 25 shows a detailed view of a measuring section for the third embodiment of the present invention.

A cross-sectional view of a measuring section 206 is shown in FIG. 25. In the third embodiment, an LED is used as the light source. In the LED package 301, two LED elements are enclosed to allow for emitting light at two wavelengths. Wavelength dispersion by grating is not applied. By modulating the outputs of the two LED elements by different frequencies, light is received by one photodiode. The received light is frequency filtered and separated into components corresponding to the outputs of the LED elements, and the intensity of transmitted light for each wavelength component is measured. Light 305 emitted from the LED package 301 is condensed by an irradiation lens and hits on the transport substrate unit 200. After the light passes through a droplet of the first reaction solution 2 or second reaction solution 3, the transmitted light is received by the photodiode and measured. In the measuring section 206 along the fluid channel 205A, the LED emitting light at wavelengths of 700 nm and 570 nm is used as the light source 301, the absorbance of light at a wavelength of 570 nm is measured in reference to 700 nm, and lipase is assayed. In the measuring section 206 along the fluid channel 205B, the LED emitting light at wavelengths of 700 nm and 600 nm is used as the light source 301, the absorbance of light at a wavelength of 600 nm is measured in reference to 700 nm, and cholesterol is assayed. In the measuring section 206 along the fluid channel 205C, the LED emitting light at wavelengths of 800 nm and 600 nm is used as the light source 301, the absorbance of light at a wavelength of 600 nm is measured in reference to 800 nm, and C-reactive protein is assayed. While the intensity of transmitted light is measured in this embodiment, the intensity of light emitted from a droplet of the first reaction solution 2 or second reaction solution 3 may be measured by the photodiode without using the light source 301.

The procedure of measuring operation will be described. To assay three substances, using one sample, an initial sample droplet is divided into three parts having equal doses by a specific method of applying voltage to the electrodes in the inlet. Droplets as these parts are serially transported through the fluid diversion section 205W and distributed to each fluid channel. By sequentially transporting such droplets, absorbance is measured in the measuring sections along each fluid channel. The mixing and measuring processes along each fluid channel are the same as described for the second embodiment. Second reaction solution 3 droplets which were subjected to the measurements pass through the fluid convergence section 205W' and are transported to the outlet 204 from which they are ejected to the ejection tank placed outside. The construction of the outlet 204 is the same as described for the second embodiment 2.

A sample droplet is inserted every 10 seconds and it takes one minute for the droplet to arrive at the first measuring section 206, 10 minutes for the droplet to pass from the first measuring section 206 to the last measuring section 206, and one minute for the droplet to pass from the last measuring section 206 to the outlet 204. It takes a total of 12 minutes to complete the analytic process for one sample droplet. Time required for the analysis of 40 sample droplets is about 18.6 minutes (40 droplets×10 sec+12 min=400 sec+12 min≈18.6 min). Because three parallel fluid channels are provided and parallel processing is performed in this embodiment, the analysis for 120 sample droplets can be performed during the above time. Analysis can be carried out at a throughput, three times higher than the second embodiment.

For the measurements performed along each fluid channel, the same results can be obtained as for the second embodiment. That is, because absorbance change with time, measured by the measuring sections 206b, is proportional to concentration, by measuring absorbance change with time for samples transported along each fluid channel, the concentration of a substance that is assayed along a fluid channel in each sample can be measured.

A fourth embodiment will be described below. In the fourth embodiment, a solution including fluorescently-labeled DNA fragments is used as a sample liquid and analysis is intended to measure the concentration of the DNA fragments in a sample liquid.

Figure 26:
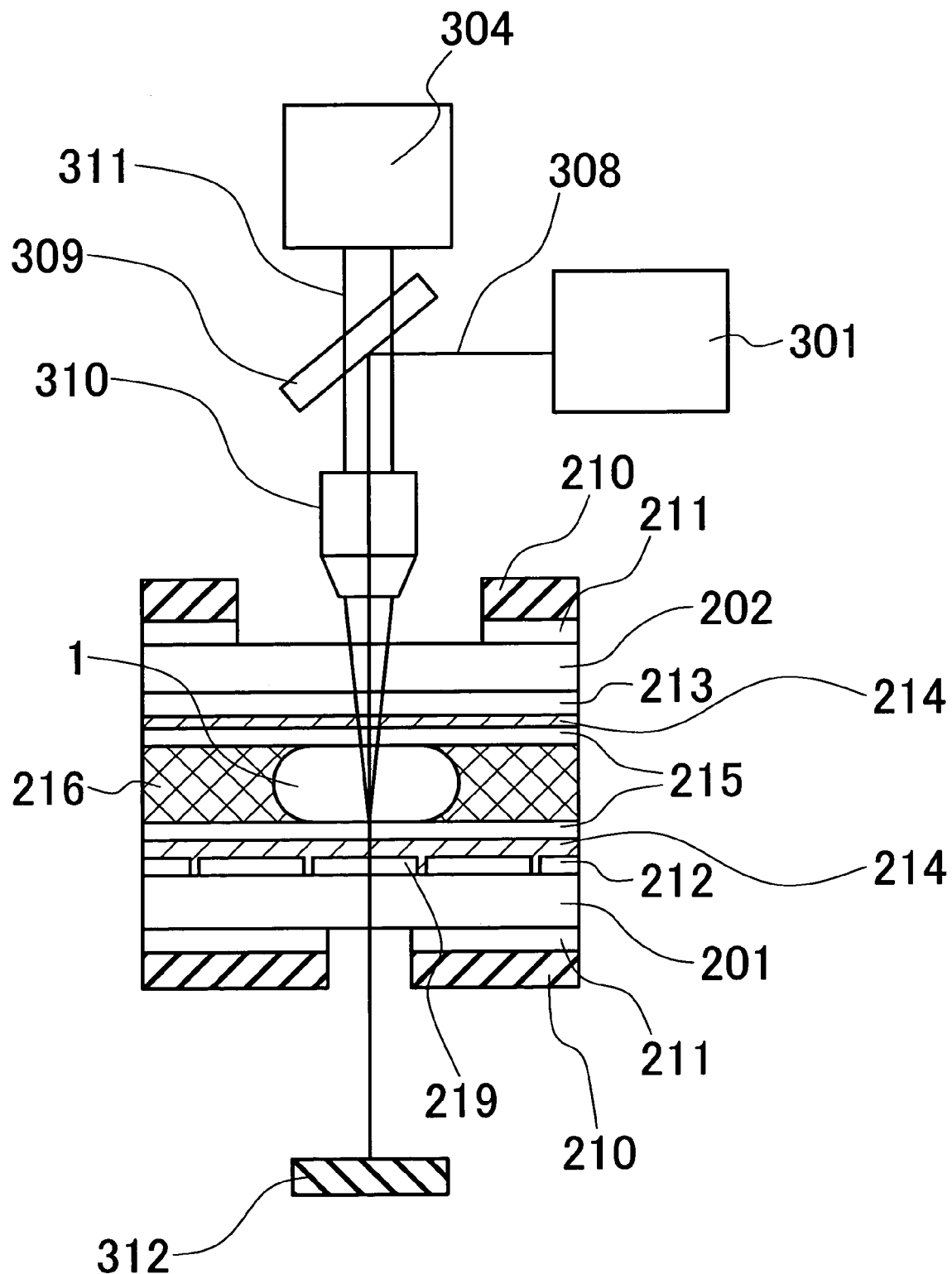
FIG. 26 shows a detailed view of a measuring section for a fourth embodiment of the present invention.

The apparatus setup and operation procedure for this embodiment are the same as described for the first embodiment. However, difference lies only in the construction of a measuring section 206 inside the transport substrate unit 200. The construction of a measuring section 206 for this embodiment is shown in FIG. 26. Laser light 308 emitted from the light source 301 is reflected by a dichroic mirror 309 and the reflected light passes through a microscopic lens 310 and hits on a sample droplet 1 above an electrode 219 in the measuring section inside the transport substrate unit 200. As the laser light source, Sapphire 488-20 from Coherent is used. FAM-labeled DNA is used as a sample. A dichroic mirror that reflects light with a wavelength less than 520 nm and transmits light at 520 nm or more is employed. For security, the laser light 308 is applied to a laser stopper 312 to prevent leakage to outside. Fluorescence 311 emitted from a liquid droplet is collected by the microscopic lens 310, transmitted through the dichroic mirror, received by a photodiode in the measuring instrument 304, and analyzed by using a PC for analysis. The operation procedure is the same as described for the first embodiment. While the laser light is focused on a single point of measurement, it is possible to apply the laser to a plurality of points by dividing the laser light 308 with half mirrors or the like and observe fluorescence emitted from the points.

In accordance with the foregoing embodiments, the present invention can also be constituted as follows.

(1) A liquid transport substrate including a first substrate set in a substantially horizontal position, wherein a plurality of electrodes are arranged on the substrate, the substrate including the electrodes is covered by an insulation film, the surface of which is rendered water-repellent, wherein a first liquid droplet is supplied to be placed above a part of the plurality of electrodes of the first substrate and transported by applying voltage to part of the plurality of electrodes and sequentially switching one electrode to another to which voltage is applied or a liquid transport substrate further including a second substrate whose under surface is all covered by an electrode, the surface of the substrate including the electrode being covered by an insulation film, the surface of which is rendered water-repellent, wherein the first substrate and the second substrate are held substantially in parallel such that their electrode sides oppose each other, separated across a given gap, wherein a first liquid droplet is supplied between the two substrates to be placed on the first substrate and above a part of the plurality of electrodes and transported by applying voltage between the electrode of the second substrate and a part of the electrodes of the first substrate and sequentially switching one electrode to another to which voltage is applied on the first substrate side, the liquid transport substrate comprising a fluid channel formed along an array of the plurality of electrodes for transporting a liquid droplet, an inlet from which the first liquid droplet is inserted into the fluid channel, an outlet from which the first liquid droplet is ejected out of the fluid channel, a measuring section for measuring information from the first liquid droplet, located in the middle of the fluid channel, and an electrical conduction means to apply voltage for actuating the transport of the first liquid droplet to each of the plurality of electrodes, wherein the measuring section is located between the inlet and the outlet.

(2) The liquid transport substrate as recited in item (1), wherein the first liquid droplet is transported from the inlet through the measuring section to the outlet in one direction.

(3) The liquid transport substrate as recited in item (1), wherein both a fluid channel segment from the inlet to the measuring section and a fluid channel segment from the measuring section to the outlet do not include a two-way passage.

(4) The liquid transport substrate as recited in item (1), wherein the first liquid is a liquid including a biochemical substance such as serum, DNA, RNA, and protein, a liquid including a chemical substance which reacts with a biochemical substance, or a liquid including a calibration substance for calibrating a measuring instrument.

(5) The liquid transport substrate as recited in item (1), wherein space above the first substrate or space between the first substrate and the second substrate is filled with gas, silicon oil as a second liquid, or fluorocarbon oil as the second liquid and a first liquid droplet is transported through the interstitial material of gas, silicon oil, or fluorocarbon oil.

(6) The liquid transport substrate as recited in item (1), wherein the electrode layer of first substrate and the electrode layer of the second substrate are reversed.

(7) The liquid transport substrate as recited in item (5), wherein the second liquid is fluorocarbon oil and the electrode layer of first substrate and the electrode layer of the second substrate are reversed.

(8) The liquid transport substrate as recited in item (1), wherein the first substrate and the second substrate are made of glass, silicon, or ceramic.

(9) The liquid transport substrate as recited in item (1), wherein a plurality of measuring sections are located on the fluid channel.

(10) The liquid transport substrate as recited in item (1), including a plurality of fluid channels including measuring sections, fluid diversion sections to distribute sample droplets, coupling the inlet to the plurality of fluid channels, and fluid convergence sections to converge, coupling the fluid channels to the outlet.

(11) The liquid transport substrate as recited in item (10), wherein the speed of transporting first liquid droplets through the plurality of fluid channels is different from the speed of transporting droplets through the fluid diversion sections and through the fluid convergence sections.

(12) The liquid transport substrate as recited in item (1), wherein means for measuring information from first liquid droplets measures the attenuation, emission intensity, or fluorescence emission intensity of transmitted light at one or a plurality of wavelengths.

(13) The liquid transport substrate as recited in item (10), wherein the means for measuring information from first liquid droplets measures the attenuation, emission intensity, or fluorescence emission intensity of transmitted light at one or a plurality of wavelengths.

(14) The liquid transport substrate as recited in item (13), wherein, when measuring light transmitted through first liquid droplets, the transmitted light at a different wavelength is measured along each of the plurality of fluid channels.

(15) The liquid transport substrate as recited in item (13), wherein a light source to apply irradiation light to first liquid droplets consists of one or a plurality of light emitting diodes.

(16) The liquid transport substrate as recited in item (1), wherein the fluid channel includes one or a plurality of mixing sections to mix the first liquid with a third liquid which dilutes the first liquid or reacts with the first liquid.

(17) The liquid transport substrate as recited in item (1), wherein an inlet hole through which a pipetter can be inserted to dispense the first liquid droplet is provided in the inlet of the liquid transport substrate.

(18) The liquid transport substrate as recited in item (1), wherein the first liquid droplet is separated into parts in the inlet and the separated liquid droplet is fed into the fluid channel by applying voltage to an electrode located under the first liquid droplet.

(19) The liquid transport substrate as recited in item (1), wherein a part of the fluid channel adjoining the outlet of the first substrate or a part of the fluid channel in the outlet is sloped horizontally toward the forward direction of the liquid droplet.

(20) The liquid transport substrate as recited in item (10), wherein a part of the fluid convergence section adjoining the outlet of the first substrate or a part of the fluid convergence section in the outlet is sloped horizontally toward the forward direction of the liquid droplet.

(21) The liquid transport substrate as recited in item (1), including thermal regulating layers and thermal insulations to keep the liquid transport substrate, the first liquid, the second liquid, and the third liquid at a constant temperature.

(22) The liquid transport substrate as recited in item (1), wherein first liquid droplets are advanced in steps of two electrodes apart, moving sequentially, through the fluid channel.

(23) The liquid transport substrate as recited in item (1), including the electrical conduction means in which wiring is made to apply voltage to one of every three electrodes synchronously.

(24) The liquid transport substrate as recited in item (1), including the electrical conduction means in which parallel wiring is made to apply voltage to the electrodes in corresponding positions of the plurality of fluid channels synchronously.

An analysis method of the present invention can also be built as follows.

(1) An analysis method comprising the steps of:
inserting a first liquid droplet into a liquid inlet;
transporting the first liquid droplet through a fluid channel by applying voltage to at least a part of a plurality of electrodes arranged along the fluid channel;
assaying the first liquid in a measuring section located on at least a segment of the fluid channel; and
ejecting the first liquid droplet from an ejection outlet,
wherein the transporting step sequentially switches one electrode to another to which the voltage is applied.

(2) The analysis method as recited in item (1), wherein the first liquid droplet is supplied between a first substrate and a second substrate and the voltage is applied between at least a part of the plurality of electrodes provided on the first substrate and an electrode layer provided on the second substrate.

(3) The analysis method as recited in item (1), wherein the first liquid droplet is transported from the liquid inlet to the measuring section and from the measuring section to the ejection outlet substantially in one direction.

(4) The analysis method as recited in item (1), wherein the fluid channel consists of a first channel from the inlet to the measuring section and a second channel from the measuring section to the outlet and the first channel and the second channel do not include a two-way passage.

(5) The analysis method as recited in item (1), wherein the fluid channel comprises a plurality of shunt channels including measuring sections in at least a segment thereof, fluid diversion sections coupling the inlet to the plurality of shunt channels, and fluid convergence sections coupling the plurality of shunt channels to the outlet.

(6) The analysis method as recited in item (1), wherein the speed of transporting first liquid droplets through the shunt channels is different from the speed of transporting droplets through the fluid convergence sections.

(7) The analysis method as recited in item (1), wherein the assaying step measures light transmitted through the first liquid droplet during light irradiation onto the measuring section, emission intensity in the measuring section, or fluorescence emission intensity in the measuring section.

(8) The analysis method as recited in item (5), wherein, in each of measuring sections located along the shunt channels, the droplet is irradiated with light at a different wavelength and transmitted light at a different wavelength is measured.

(9) The analysis method as recited in item (1), wherein the fluid channel includes a mixing section to mix a plurality of liquids in at least a segment thereof.

(10) The analysis method as recited in item (1), wherein the liquid inlet includes a plurality of electrodes in the inlet and the first liquid droplet is separated into parts and a separated droplet is transported into the fluid channel by applying voltage to at least a part of the electrodes in the inlet.

(11) The analysis method as recited in item (1), wherein the plurality of electrodes hold first liquid droplets above them two electrodes apart and the first liquid droplets are sequentially moved by switching one electrode to another to which voltage is applied.

What is claimed is:

1. A liquid transport substrate comprising:
a first substrate;
an inlet into which a liquid droplet is inserted, provided on said first substrate;
an outlet from which said liquid droplet is ejected, provided on said first substrate;
a plurality of electrodes provided on said first substrate; and
an electrical conduction means to apply voltage at least a part of said plurality of electrodes, wherein said plurality of electrodes form a fluid channel through which liquid droplets are transported as a result of a voltage application by said electrical conduction means and a measuring section, wherein said fluid channel lies between said inlet and said outlet and said measuring section is located on at least a segment of said fluid channel,
wherein said fluid channel at said outlet and/or a part of said fluid channel adjoining said outlet is open from above to outside of said liquid transport substrate and has ascending and descending slopes.

2. The liquid transport substrate according to claim 1, further comprising a first insulation film covering said plurality of electrodes and a first film covering said insulation film.

3. The liquid transport substrate according to claim 1, further comprising:
a second substrate; and
a electrode layer provided on said second substrate,
wherein said plurality of electrodes and said electrode layer oppose each other.

4. The liquid transport substrate according to claim 3, further comprising a second insulation film covering said electrode layer and a second film covering said second insulation film.

5. The liquid transport substrate according to claim 3, wherein said plurality of electrodes and said electrode layer are placed substantially in parallel.

6. The liquid transport substrate according to claim 3, wherein said first substrate and said second substrate are placed so that said plurality of electrodes and said electrode layer are separated across a given gap.

7. The liquid transport substrate according to claim 1, wherein said fluid channel comprises a first channel from said inlet to said measuring section and a second channel from said measuring section to said outlet and said first channel and said second channel do not include a two-way passage.

8. The liquid transport substrate according to claim 1, wherein said liquid is at least any of a biochemical substance, a chemical substance which reacts with said biochemical substance, and a calibration substance.

9. The liquid transport substrate according to claim 3, wherein said first substrate and said second substrate are made of at least any of glass, silicon, and ceramic.

10. The liquid transport substrate according to claim 1, including a plurality of measuring sections.

11. The liquid transport substrate according to claim 1, wherein said fluid channel comprises a plurality of shunt channels including measuring sections in at least a segment thereof, fluid diversion sections coupling said inlet to said plurality of shunt channels, and fluid convergence sections coupling said plurality of shunt channels to said outlet.

12. The liquid transport substrate according to claim 1, wherein said fluid channel includes a mixing section to mix a plurality of liquids, one of which is said liquid.

13. The liquid transport substrate according to claim 11, wherein the shunt channels are arranged separately for each substance to be assayed, said outlet includes electrodes in the outlet and a part of said fluid channel adjoining said outlet and/or said outlet is sloped horizontally.

14. The liquid transport substrate according to claim 1, further comprising thermal regulating layers and thermal insulations near said first substrate.

15. The liquid transport substrate according to claim 1, wherein said electrical conduction means includes wiring to apply a synchronous voltage to one of every three electrodes among said plurality of electrodes.

16. A liquid transport substrate comprising:

a first substrate;

a fluid channel provided on said substrate which is at least partly filled with an interstitial material;

said fluid channel having an inlet into which liquid droplets are inserted and an outlet from which the liquid droplets are ejected;

a plurality of electrodes provided on said first substrate; and a measuring section, wherein said fluid channel lies between said inlet and said outlet and said measuring section is located on at least a segment of said fluid channel, wherein said plurality of electrodes transport said droplets along said fluid channel between said inlet and said outlet, and wherein said fluid channel is open from above to outside of said liquid transport substrate and has an ascending sloped portion along which said droplets are transported by said plurality of electrodes to at least partly above a level of said interstitial material in said fluid channel.

17. The liquid transport substrate according to claim 16, wherein said fluid channel has a descending sloped portion adjacent said ascending sloped portion at said outlet of said fluid channel to transport said droplets from said ascending sloped portion to said outlet.

18. The liquid transport substrate according to claim 16, wherein said interstitial material is one of silicon oil and fluorocarbon oil.

* * * * *